United States Patent
Cohen et al.

(10) Patent No.: US 12,227,806 B2
(45) Date of Patent: **\*Feb. 18, 2025**

(54) METHODS FOR DETECTING AN INCREASED RISK FOR CORONARY HEART DISEASE

(71) Applicant: Board of Regents, The University of Texas System, Dallas, TX (US)

(72) Inventors: Jonathan C. Cohen, Dallas, TX (US); Helen H. Hobbs, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 111 days.

This patent is subject to a terminal disclaimer.

(21) Appl. No.: 17/472,740

(22) Filed: Sep. 13, 2021

(65) Prior Publication Data

US 2022/0177969 A1     Jun. 9, 2022

Related U.S. Application Data

(63) Continuation of application No. 15/810,059, filed on Nov. 11, 2017, now abandoned, which is a continuation of application No. 13/907,923, filed on Jun. 2, 2013, now abandoned, which is a continuation of application No. 12/151,275, filed on May 2, 2008, now abandoned.

(60) Provisional application No. 60/927,361, filed on May 2, 2007.

(51) Int. Cl.
   *C12Q 1/68*     (2018.01)
   *C12Q 1/6883*     (2018.01)

(52) U.S. Cl.
   CPC ..... *C12Q 1/6883* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 7,883,851 B2 * | 2/2011 | Cohen | C12Q 1/6883 435/91.2 |
| 2010/0068705 A1 * | 3/2010 | Helgadottir | A61P 9/00 435/6.1 |

OTHER PUBLICATIONS

Leor et al. (J Am Coll Cardiol 1999;33:1920 -5) (Year: 1999).*
Cleveland Clinic. Congestive Heart Failure. Obtained from https://my.clevelandclinic.org/health/diseases/17069-heart-failure-understanding-heart-failure on Feb. 9, 2024, 19 pages (Year: 2024).*
Wang et al. Am. J. Hum. Genet. 74:262-271, 2004 (Year: 2004).*

* cited by examiner

*Primary Examiner* — Juliet C Switzer
(74) *Attorney, Agent, or Firm* — Richard Aron Osman

(57) ABSTRACT

The invention relates generally to an allele on human chromosome 9 associated with increased risk for coronary heart disease and the use or detection of such an allele in determining whether a human has an increased risk for coronary heart disease. In one aspect, the invention relates to methods for detecting a predisposition or propensity or susceptibility for coronary heart disease in a human, comprising detecting the presence of an allele on human chromosome 9 that is associated with an increased risk for coronary heart disease in a human. Disclosed are methods and compositions for determining whether a person carries an allele associated with increased risk for coronary atherosclerosis by determining whether the person has an RA-CHR9 allele, such as by determining whether the person has an RA-CHR9 allele-associated single nucleotide polymorphism (SNP). The invention also relates to kits for detecting the presence of an allele on chromosome 9 associated with an increased risk for coronary heart disease.

4 Claims, 2 Drawing Sheets

Screening

Genome-wide Association Scan (75,000 SNPs/person)

Ottawa Heart Study-1 (OHS-1)

322 Cases : 312 controls

Replicate Association Study 1: SNPs with P <0.025

Ottawa Heart Study-2 (OHS-2)

311 cases : 326 controls

Replicate Association Study 2: SNPs with P <0.025

Atherosclerosis Risk in Communities Study (ARIC)

1,347 cases : 9,054 controls

rs10757274 and rs2383206

Validation

| Copenhagen City Heart Study (CCHS) | Dallas Heart Study (DHS) | Ottawa Heart Study-3 (OHS-3) |
|---|---|---|
| 1,525 cases | 154 cases | 618 cases |
| 9,053 controls | 527 controls | 782 controls |

FIG. 1

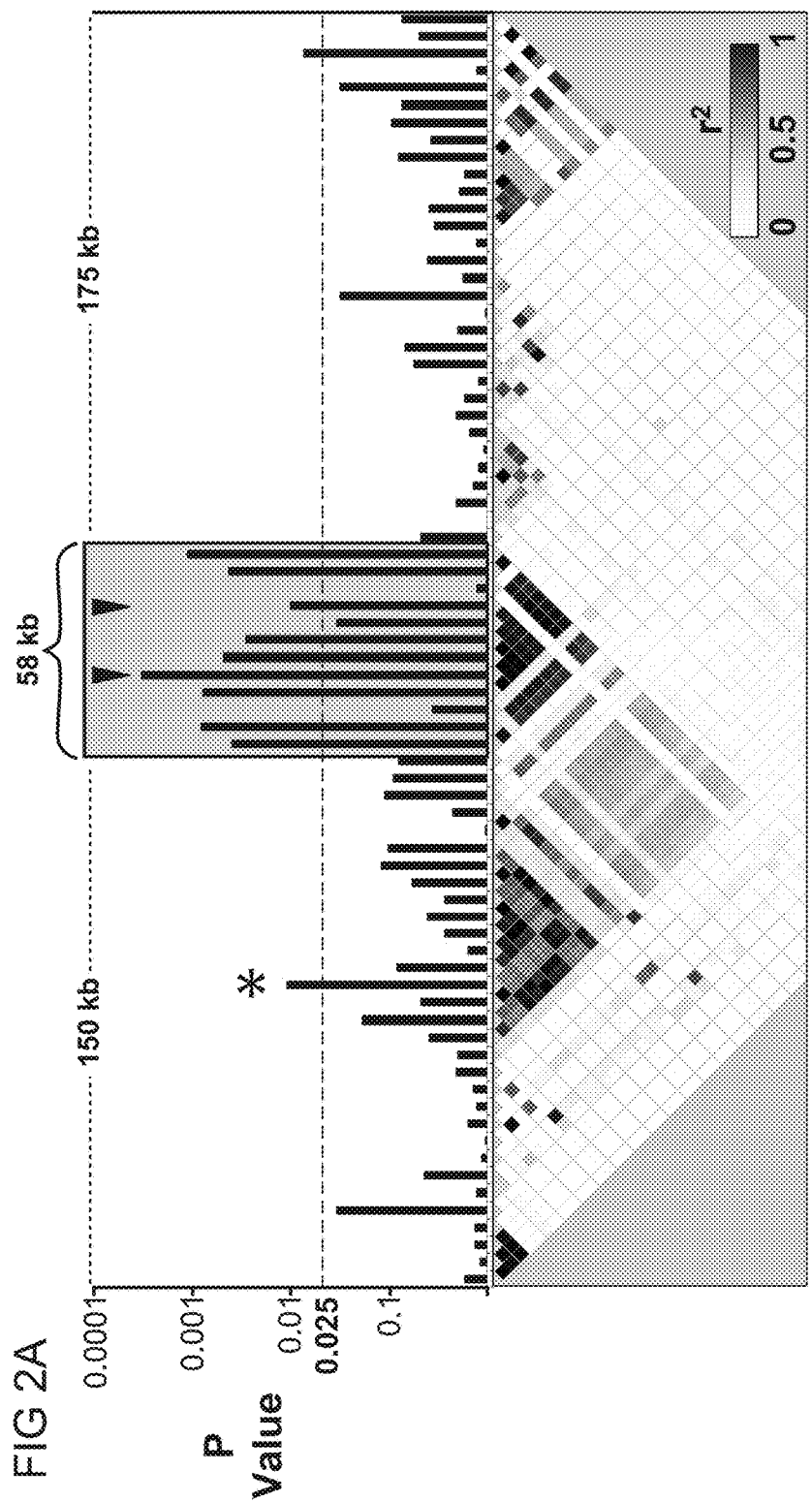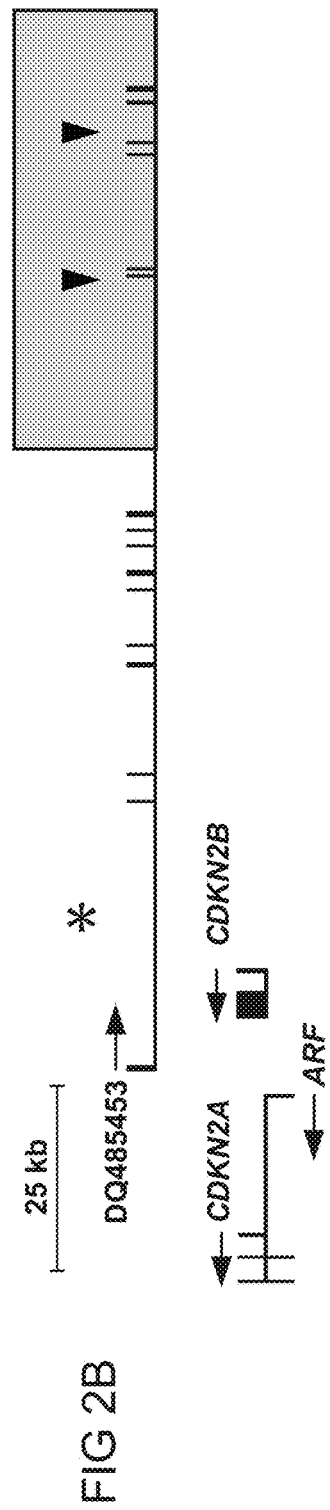
FIG 2A
FIG 2B

METHODS FOR DETECTING AN INCREASED RISK FOR CORONARY HEART DISEASE

This application claims priority benefit to U.S. provisional patent application Ser. No. 60/927,361, filed May 2, 2007, which is incorporated herein by reference in its entirety.

1. INTRODUCTION

The invention relates generally to an allele on human chromosome 9 associated with increased risk for coronary heart disease and the use or detection of such an allele in determining whether a human has an increased risk for coronary heart disease. In one aspect, the invention relates to methods for detecting a predisposition or propensity or susceptibility for coronary heart disease in a human, comprising detecting the presence of an allele on human chromosome 9 that is associated with an increased risk for coronary heart disease in a human. The invention also relates to kits for detecting the presence of an allele on chromosome 9 associated with an increased risk for coronary heart disease.

2. BACKGROUND OF THE INVENTION

Coronary heart disease (CHD) is the single greatest cause of death worldwide (Murray et al. (1997) Lancet 349: 1436; Mathers et al. (2006) PLoS Med. 3: e442). Coronary heart disease is a complex disease. The identification of genetic markers associated with increased risk for coronary heart disease can be used to develop and implement strategies to treat and to reduce the likelihood of a human developing coronary heart disease.

3. SUMMARY OF THE INVENTION

In one aspect, the invention provides methods and compositions for determining whether a person carries an allele associated with increased risk for coronary heart disease (e.g., coronary atherosclerosis or myocardial infarction) by determining whether the person has an RA-CHR9 allele. In certain embodiments, the RA-CHR9 allele is an approximately 58 kb region extending from about position 22,062,301 to about position 22,120,389 of human chromosome 9 that is significantly associated with coronary heart disease. In a specific embodiment, the RA-CHR9 allele is a 58 kb region extending from 22,062,301 to 22,120,389 of human chromosome 9 that is significantly associated with coronary heart disease. In particular embodiments, the person has a family history of coronary atherosclerosis. In some embodiments, the person has a family history of myocardial infarction.

In one embodiment, the invention provides a method for determining whether a person carries an allele associated with increased risk for coronary heart disease, the method comprising using an in vitro assay to detect whether the person has an RA-CHR9 allele. In a specific embodiment, the invention provides a method for determining whether a person carries an allele associated with increased risk for coronary heart disease, the method comprising detecting one, two, three or more, all or any combination of the single nucleotide polymorphisms ("SNPs") found in an RA-CHR9 allele, such as those SNPs in Table 7, Table 8, Table 10 or Table 11. Non-limiting examples of SNPs found in an RA-CHR9 allele include those SNPs found at the following positions on human chromosome 9: the SNP found at position 22062301; the SNP found at position 22062638; the SNP found at position 22067543; the SNP found at position 22062719; the SNP found at position 22071397; the SNP found at position 22071850; the SNP found at position 22078090; the SNP found at position 22078094; the SNP found at position 22078260; the SNP found at position 22086055; the SNP found at position 22088574; the SNP found at position 22088619; the SNP found at position 22090176; the SNP found at position 22091702; the SNP found at position 22092165; the SNP found at position 22093183; the SNP found at position 22093341; the SNP found at position 22093813; the SNP found at position 22095927; the SNP found at position 22096731; the SNP found at position 22100131; the SNP found at position 22102241; the SNP found at position 22102427; the SNP found at position 22104469; the SNP found at position 22104495; the SNP found at position 22105026; the SNP found at position 22105286; the SNP found at position 22106046; the SNP found at position 22106220; the SNP found at position 22113766; the SNP found at position 22114123; the SNP found at position 22114140; the SNP found at position 22115347; and the SNP found at position 22115503. In a specific embodiment, the SNPs at rs10757274 and rs2383206 are detected.

In another embodiment, the invention provides a method for determining whether a person carries an allele associated with increased risk for coronary heart disease, the method comprising detecting one, two, three or more, all or any combination of the insertions and/or deletions found in an RA-CHR9 allele, such as those insertions and/or deletions in Table 7 or 10. Non-limiting examples of insertions and deletions in an RA-CHR9 allele include those insertions and deletions found at the following positions on human chromosome 9: the deletion found at position 22078465; the insertion found at position 22089755; the insertion found at position 22101587; and the insertion found at position 22110491.

In another embodiment, the invention provides a method for determining whether a person carries an allele associated with increased risk for coronary heart disease, the method comprising detecting one, two, three or more, all or any combination of the SNPs, insertions and/or deletions found in an RA-CHR9 allele, such as those insertions and/or deletions in Table 7, Table 8, Table 10 or Table 11. Non-limiting examples of SNPs, insertions and deletions found in an RA-CHR9 allele include those SNPs, insertions and deletions found at the following positions on human chromosome 9: the SNP found at position 22062301; the SNP found at position 22062638; the SNP found at position 22062719; the SNP found at position 22071397; the SNP found at position 22071850; the SNP found at position 22078090; the SNP found at position 22078094; the SNP found at position 22078260; the deletion found at position 22078465; the SNP found at position 22086055; the SNP found at position 22088574; the SNP found at position 22088619; the insertion found at position 22089755; the SNP found at position 22090176; the SNP found at position 22091702; the SNP found at position 22092165; the SNP found at position 22093183; the SNP found at position 22093341; the SNP found at position 22093813; the SNP found at position 22095927; the SNP found at position 22096731; the SNP found at position 22100131; the insertion found at position 22101587; the SNP found at position 22102241; the SNP found at position 22102427; the SNP found at position 22104469; the SNP found at position 22104495; the SNP found at position 22105026; the SNP found at position 22105286; the SNP found at position 22106046; the SNP found at position 22106220; the insertion found at position 22110491; the SNP found at position 22113766; the SNP found at position 22114123; the SNP found at position 22114140; the SNP found at position 22115347; and the SNP found at position 22115503.

In another embodiment, the invention provides a method for determining whether a person carries an allele associated with increased risk for coronary atherosclerosis, the method comprising using an in vitro assay to detect whether the person has an RA-CHR9 allele. In another embodiment, the invention provides a method for determining whether a person carries an allele associated with increased risk for coronary atherosclerosis, the method comprising the step of: determining whether the person has an RA-CHR9 allele. In certain embodiments, the determining step comprises detecting one, two, three or more or all of the single nucleotide polymorphisms (SNPs) found in an RA-CHR9 allele, such as those SNPs in Table 7, Table 8, Table 10 or Table 11. In particular embodiments, the determining step comprises detecting the allele using a method selected from the group consisting of: mass spectroscopy, oligonucleotide microarray analysis, allele-specific hybridization, allele-specific PCR, and sequencing.

In another embodiment, the invention provides a method for determining whether a person carries an allele associated with increased risk of having a myocardial infarction, the method comprising using an in vitro assay to detect whether the person has an RA-CHR9 allele. In a specific embodiment, the invention provides a method for determining whether a person carries an allele associated with increased risk of having a myocardial infarction, the method comprising detecting in vitro one, two, three or more or all of the single nucleotide polymorphisms (SNPs) found in an RA-CHR9 allele, such as those SNPs in Table 7, Table 8, Table 10 or Table 11.

In another aspect, the invention provides a method for identifying a human subject at increased risk for coronary heart disease, comprising using an in vitro assay to detect the presence of a risk allele in an approximately 58 kb region extending from approximately 22,062,301 to approximately 22,120,389 of human chromosome 9 in a human subject that is more frequently present in a population of humans with coronary heart disease than in a population of humans that do not have coronary heart disease, wherein the presence of the risk allele indicates that the human subject has an increased risk for coronary heart disease. In certain embodiments, the risk allele is in a region extending from position 22,062,201+/−5808, 5000, 4000, 3000, 2500, 2000, 1500, 1101, 1000, 550, 500, 450, 400, 350, 300, 250, 200, 150, 100 or 50 nucleotides to position 22,120,389+/−5808, 5000, 4000, 3000, 2500, 2000, 1500, 1101, 1000, 550, 500, 450, 400, 350, 300, 250, 200, 150, 100 or 50 nucleotides of human chromosome 9. In a specific embodiment, the risk allele is in a region extending from position 22,062,201 to position 22,120,389 of human chromosome 9. In certain embodiments, the risk allele is at a position on human chromosome 9 identified in Table 7, Table 8, or Table 10 or Table 11. In one embodiment, the risk allele is at least one of the following positions on human chromosome 9: position 22062301; position 22062638; position 22067543; position 22062719; position 22071397; position 22071850; position 22078090; position 22078094; position 22078260; position 22078465; position 22086055; position 22088574; position 22088619; position 22089755; position 22090176; position 22091702; position 22092165; position 22093183; position 22093341; position 22093813; position 22095927; position 22096731; position 22100131; position 22101587; position 22102241; position 22102427; position 22104469; position 22104495; position 22105026; position 22105286; position 22106046; position 22106220; position 22110491; position 22113766; position 22114123; position 22114140; position 22115347; and/or position 22115503. In another embodiment, the risk allele is at one or more, all or any combination of the following: rs9632884, rs6475606, rs10757272, rs10757274, rs4977574, rs2891168, rs1333042, rs2383206, rs1333048, or rs1333049. In a specific embodiment, the risk allele is at rs10757274 or rs2383206. In another specific embodiment, the risk alleles are rs10757274 and rs2383206.

In another aspect, the invention provides a method for identifying a human subject at increased risk for coronary heart disease, comprising using an in vitro assay to detect the presence of a human chromosome 9 haplotype comprising a guanine nucleotide at position 22086055 (rs10757274) and/or a guanine at position 22105026 (rs2383206) in a human subject, wherein the presence of the haplotype indicates that the human subject has an increased risk for coronary heart disease. In one embodiment, the haplotype comprises a guanine nucleotide at position 22086055 (rs10757274) and a guanine nucleotide at position 22105026 (rs2383206) of chromosome 9. In another embodiment, the haplotype comprises a guanine nucleotide at position 22086055 (rs10757274) and/or a guanine nucleotide at position 22105026 (rs2383206), and at least one, two, three, or more, all or any combination of the following SNPs: a cytosine nucleotide at position 22062301 (rs9632884), a thymine nucleotide at position 22071850 (rs6475606), a thymine nucleotide at position 22078260 (rs10757272), a guanine at position 22088574 (rs4977574), a guanine nucleotide at position 22088619 (rs2891168), a guanine nucleotide at position 22093813 (rs1333042), a cytosine nucleotide at position 22115347 (rs1333048), and/or a cytosine nucleotide at position 22115503 (rs1333049). In another embodiment, the haplotype comprises guanine nucleotide at position 22086055 (rs10757274) and/or a guanine nucleotide at position 22105026 (rs2383206), and at least one, two, three or more, all or any combination of the following: a guanine nucleotide at position 22062264; a cytosine nucleotide at position 22062301; an adenine nucleotide at position 22062638; a guanine nucleotide at position 22062719; a thymine nucleotide at position 22071397; a thymine nucleotide at position 22071850; a thymine nucleotide at position 22078090; a guanine nucleotide at position 22078094; a thymine nucleotide at position 22078260; a deletion at position 22078465; a guanine nucleotide at position 2208874; a guanine nucleotide at position 22088619; an insertion at position 22089755; a cytosine nucleotide position 22090176; a cytosine nucleotide at position 22091702; a thymine nucleotide at position 22092165; a thymine nucleotide at position 22093183; a guanine nucleotide at position 22093341; a guanine nucleotide at position 22093813; a cytosine nucleotide at position 22095927; an adenine nucleotide at position 22096731; a cytosine nucleotide at position 22100131; an insertion at position 22101587; a cytosine nucleotide at position 22102241; a guanine nucleotide at position 22102427; a cytosine nucleotide at position 22104469; a guanine nucleotide at position 22104495; a cytosine nucleotide at position 22105286; a guanine nucleotide at position 22106046; a cytosine nucleotide at position 22106220; an insertion at position 22110491; a cytosine nucleotide at position 22113766; an adenine nucleotide at position 22114123; a thymine nucleotide at position 22114140; a cytosine nucleotide at position 22115347; and/or a cytosine at position 22115503. In a specific embodiment, the haplotype is in a region extending from position 22062301 to 22120389 of human chromosome 9.

In another aspect, the invention provides a method for identifying a human subject at increased risk for coronary heart disease, comprising using an in vitro assay to detect the presence of a polymorphism with a linkage disequilibrium of between 0.5 to 1, 0.5 to 0.90, or 0.5 to 0.80, or 0.5 to 0.75 with a risk allele in an approximately 58 kb region extending from approximately 22,062,301 to approximately 22,120,389 of human chromosome 9 in a human subject, wherein the presence of the polymorphism indicates that the human subject has an increased risk for coronary heart disease. In certain embodiments, the presence of a polymorphism with a linkage disequilibrium of at least $r^2$=0.50, 0.55, 0.60, 0.65, 0.70, 0.75, 0.80, or 0.85 with a risk allele in an approximately 58 kb region extending from about 22,062,301 to about 22,120,389 of human chromosome 9 in a human subject is detected. In some embodiments, a polymorphism with a linkage disequilibrium of at least $r^2$=0.89, 0.90, 0.91, 0.92, 0.93, 0.94, 0.95, 0.96, 0.97, 0.98 or 0.99 with a risk allele in an approximately 58 kb region extending from about 22,062,301 to about 22,120,389 of human chromosome 9 in a human subject is detected. In a specific embodiment, a polymorphism with a linkage disequilibrium of $r^2$=0.89, 0.90, 0.91, 0.92, 0.93, 0.94, 0.95, 0.96, 0.97, 0.98, 0.99 or 1 with a risk allele in an approximately 58 kb region extending from about 22,062,301 to about 22,120,389 of human chromosome 9 in a human subject is detected. In certain embodiments, the risk allele is in a region extending from position 22,062,301+/−5808, 5000, 4000, 3000, 2500, 2000, 1500, 1101, 1000, 550, 500, 450, 400, 350, 300, 250, 200, 150, 100 or 50 nucleotides to position 22,120,389+/− 5808, 5000, 4000, 3000, 2500, 2000, 1500, 1101, 1000, 550, 500, 450, 400, 350, 300, 250, 200, 150, 100 or 50 nucleotides of human chromosome 9. In a specific embodiment, the risk allele is in a region extending from position 22,062,301 to position 22,120,389 of human chromosome 9.

In another aspect, the invention provides a method for determining whether a person carries an allele associated with increased risk for coronary heart disease (e.g., coronary atherosclerosis or myocardial infarction), comprising determining whether the person carries at least one, two, three, four or more, all or any combination of the SNPs, insertions and/or deletions listed in Table 7, Table 8, Table 10 or Table 11, wherein the presence of one, two, three, four or more, all or any combination of the SNPs indicates that the person carries an allele associated with an increased risk for coronary heart disease. In one embodiment, the invention provides a method for determining whether a person carries an allele associated with increased risk for coronary heart disease (e.g., coronary atherosclerosis or myocardial infarction), comprising determining whether the person carries at least one, two, three, four or more, all or any combination of the following SNPs, insertions and/or deletions on human chromosome 9: a guanine nucleotide at position 22062264; a cytosine nucleotide at position 22062301; an adenine nucleotide at position 22062638; a guanine nucleotide at position 22062719; a thymine nucleotide at position 22071397; a thymine nucleotide position 22071850; a thymine nucleotide position 22078090; a guanine nucleotide at position 22078094; a thymine nucleotide position 22078260; a deletion at position 22078465; a guanine nucleotide at position 22088574; a guanine nucleotide at position 22088619; an insertion at position 22089755; a cytosine nucleotide position 22090176; a cytosine nucleotide at position 22091702; a thymine nucleotide at position 22092165; a thymine nucleotide at position 22093183; a guanine nucleotide at position 22093341; a guanine nucleotide at position 22093813; a cytosine nucleotide at position 22095927; an adenine nucleotide at position 22096731; a cytosine nucleotide at position 22100131; an insertion at position 22101587; a cytosine nucleotide at position 22102241; a guanine nucleotide at position 22102427; a cytosine nucleotide at position 22104469; a guanine nucleotide at position 22104495; a guanine nucleotide at 22105026; a cytosine nucleotide at position 22105286; a guanine nucleotide at position 22106046; a cytosine nucleotide at position 22106220; an insertion at position 22110491; a cytosine nucleotide at position 22113766; an adenine nucleotide at position 22114123; a thymine nucleotide at position 22114140; a cytosine nucleotide at position 22115347; and/or a cytosine at position 22115503, wherein the presence of one, two, three, four or more, all or any combination of the SNPs, insertions and/or deletions indicates that the person carries an allele associated with an increased risk for coronary heart disease. In a specific embodiment, the SNPs detected are at rs10757274 and rs2383206.

In another embodiment, the invention provides a method for determining whether a person carries an allele associated with increased risk for coronary heart disease (e.g., coronary atherosclerosis or myocardial infarction), comprising determining whether the person carries a guanine nucleotide at position 22086055 (rs10757274) and/or a guanine nucleotide at position 22105026 (rs2383206) on human chromosome 9, and at least one, two, three, or more, all or any combination of the following SNPs on human chromosome 9: a cytosine nucleotide at position 22062301 (rs9632884), a thymine nucleotide at position 22071850 (rs6475606), a thymine nucleotide at position 22078260 (rs10757272), a guanine at position 22088574 (rs4977574), a guanine nucleotide at position 22088619 (rs2891168), a guanine nucleotide at position 22093813 (rs1333042), a cytosine nucleotide at position 22115347 (rs1333048), and/or a cytosine nucleotide at position 22115503 (rs1333049), wherein the presence of one, two, three, or more, all or any combination of the SNPs indicates that the person carries an allele associated with an increased risk for coronary heart disease. In a specific embodiment, the invention provides a method for determining whether a person carries an allele associated with increased risk for coronary heart disease (e.g., coronary atherosclerosis or myocardial infarction), comprising determining whether the person carries a guanine nucleotide at position 22086055 (rs10757274) and a guanine nucleotide at position 22105026 (rs2383206) on human chromosome 9, wherein the presence of the SNPs indicates that the person carries an allele associated with an increased risk for coronary heart disease. In another embodiment, the invention provides a method for determining whether a person carries an allele associated with an increased risk for coronary heart disease, comprising determining whether the person carries a cytosine nucleotide at position 22115503 (rs1333049) alone or in addition to one, two, three or more SNPs, insertions and/or deletions found in the approximately 58 kb region extending from about 2,062,301 to about 22,120,301 (in specific embodiments, in the region extending from position 22,062,301 to position 22,120,389) of human chromosome 9, such as those described herein (see, e.g., Table 7, Table 8, Table 10 and Table 11).

In another aspect, the invention provides a method for determining whether a human subject has an allele associated with an increased risk for coronary heart disease, comprising using an in vitro assay to detect whether a risk allele is present in the human subject, wherein the risk allele is in an approximately 58 kb region extending from approximately 22,062,301 to approximately 22,120,389 of human chromosome 9 that is more frequently present in a population of humans with coronary heart disease than in a population of humans that do not have coronary heart disease. In a specific embodiments, the risk allele is in a region extending from 22,062,301 to 22,120,389 of human chromosome 9. In certain embodiments, the risk allele is at a position on human chromosome 9 identified in Table 7, Table 8, or Table 10 or Table 11. In one embodiment, the risk allele is at least one of the following positions on human chromosome 9: position 22062301; position 22062638; position 22067543; position 22062719; position 22071397; position 22071850; position 22078090; position 22078094; position 22078260; position 22078465; position 22086055; position 22088574; position 22088619; position 22089755; position 22090176; position 22091702; position 22092165; position 22093183; position 22093341; position 22093813; position 22095927; position 22096731; position 22100131; position 22101587; position 22102241; position 22102427; position 22104469; position 22104495; position 22105026; position 22105286; position 22106046; position 22106220; position 22110491; position 22113766; position 22114123; position 22114140; position 22115347; and/or position 22115503. In another embodiment, the risk allele is at one or more, all or any combination of the following: rs9632884, rs6475606, rs10757272, rs10757274, rs4977574, rs2891168, rs1333042, rs2383206, rs1333048, or rs1333049. In a specific embodiment, the risk allele is at rs10757274 or rs2383206.

In another aspect, the invention provides a method for determining whether a human subject has a haplotype associated with increased risk for coronary heart disease, comprising using an in vitro assay to detect whether a human chromosome 9 haplotype comprising a guanine nucleotide at position 22086055 (rs10757274) and/or a guanine at position 22105026 (rs2383206) is present in a human subject. In one embodiment, the haplotype comprises a guanine nucleotide at position 22086055 (rs10757274) and a guanine nucleotide at position 22105026 (rs2383206) of chromosome 9. In another embodiment, the haplotype comprises a guanine nucleotide at position 22086055 (rs10757274) and/or a guanine nucleotide at position 22105026 (rs2383206), and at least one, two, three, or more, all or any combination of the following SNPs: a cytosine nucleotide at position 22062301 (rs9632884), a thymine nucleotide at position 22071850 (rs6475606), a thymine nucleotide at position 22078260 (rs10757272), a guanine at position 22088574 (rs4977574), a guanine nucleotide at position 22088619 (rs2891168), a guanine nucleotide at position 22093813 (rs1333042), a cytosine nucleotide at position 22115347 (rs1333048), and/or a cytosine nucleotide at position 22115503 (rs1333049). In another embodiment, the haplotype comprises guanine nucleotide at position 22086055 (rs10757274) and/or a guanine nucleotide at position 22105026 (rs2383206), and at least one, two, three or more, all or any combination of the following: a guanine nucleotide at position 22062264; a cytosine nucleotide at position 22062301; an adenine nucleotide at position 22062638; a guanine nucleotide at position 22062719; a thymine nucleotide at position 22071397; a thymine nucleotide at position 22071850; a thymine nucleotide at position 22078090; a guanine nucleotide at position 22078094; a thymine nucleotide position 22078260; a deletion at position 22078465; a nucleotide guanine at position 2208874; a guanine nucleotide at position 22088619; an insertion at position 22089755; a cytosine nucleotide position 22090176; a cytosine nucleotide at position 22091702; a thymine nucleotide at position 22092165; a thymine nucleotide at position 22093183; a guanine nucleotide at position 22093341; a guanine nucleotide at position 22093813; a cytosine nucleotide at position 22095927; an adenine nucleotide at position 22096731; a cytosine nucleotide at position 22100131; an insertion at position 22101587; a cytosine nucleotide at position 22102241; a guanine nucleotide at position 22102427; a cytosine nucleotide at position 22104469; a guanine nucleotide at position 22104495; a cytosine nucleotide at position 22105286; a guanine nucleotide at position 22106046; a cytosine nucleotide at position 22106220; an insertion at position 22110491; a cytosine nucleotide at position 22113766; an adenine nucleotide at position 22114123; a thymine nucleotide at position 22114140; a cytosine nucleotide at position 22115347; and/or a cytosine at position 22115503. In one embodiment, the haplotype is in a region extending from about position 22062301 to about position 22120389 of human chromosome 9. In certain embodiments, the haplotype is in a region extending from position 22062301+/−5808, 5000, 4000, 3000, 2500, 2000, 1500, 1101, 1000, 550, 500, 250, 200, 150, 100 or 50 nucleotides to position 2212039+/−5808, 5000, 4000, 3000, 2500, 2000, 1500, 1101, 1000, 550, 500, 250, 200, 150, 100 or 50 nucleotides of human chromosome 9. In a specific embodiment, the haplotype is in a region extending from position 22,062,301 to position 22,120,039 of human chromosome 9.

In another aspect, the invention provides a method for determining a human subject has a polymorphism associated with increased risk for coronary heart disease, comprising using in vitro assay to detect whether a polymorphism with a linkage disequilibrium of between 0.5 to 1, 0.5 to 0.90, or 0.5 to 0.80, or 0.5 to 0.75 with a risk allele in an approximately 58 kb region extending from approximately 22,062,301 to approximately 22,120,389 of human chromosome 9 is present in a human subject. In certain embodiments, the presence of a polymorphism with a linkage disequilibrium of at least $r^2$=0.50, 0.55, 0.60, 0.65, 0.70, 0.75, 0.80, or 0.85 with a risk allele in an approximately 58 kb region extending from about 22,062,301 to about 22,120,389 of human chromosome 9 in a human subject is detected. In some embodiments, a polymorphism with a linkage disequilibrium of at least $r^2$=0.89, 0.90, 0.91, 0.92, 0.93, 0.94, 0.95, 0.96, 0.97, 0.98 or 0.99 with an approximately 58 kb risk allele in a region extending from about 22,062,301 to about 22,120,389 of human chromosome 9 in a human subject is detected. In a specific embodiment, a polymorphism with a linkage disequilibrium of $r^2$=0.89, 0.90, 0.91, 0.92, 0.93, 0.94, 0.95, 0.96, 0.97, 0.98, 0.99 or 1 with a risk allele in an approximately 58 kb region extending from about 22,062,301 to about 22,120,389 of human chromosome 9 in a human subject is detected. In some embodiments, the risk allele(s) is at rs10757274 and rs2383206. In certain embodiments, the risk allele is in a region extending from position 2206301+/−5808, 5000, 4000, 3000, 2500, 2000, 1500, 1101, 1000, 550, 500, 250, 200, 150, 100, or 50 nucleotides to position 22120389+/−5808, 5000, 4000, 3000, 2500, 2000, 1500, 1101, 1000, 550, 500, 250, 200, 150, 100, or 50 nucleotides of human chromosome 9. In a specific embodiment, the risk allele is in a region extending from position 22,062,301 to position 22,120,039 of human chromosome 9.

In addition to the SNPs and other polymorphisms demonstrated herein to correlate with CHD, such as listed in e.g., Table 7, Table 8 and Table 10, in view of the teaching herein further SNPs and other polymorphisms as an indication of an increased risk of CHD that can routinely be detected/ identified. For example, additional SNPs present within the approximately 58 kb region described herein (see, e.g., the SNPs listed in Table 11) can be identified as correlation with increased risk for CHD. Routine techniques, such as genotyping and other techniques described herein can be used to identify such SNPs and other polymorphisms.

In certain embodiments, the methods further comprise providing results, information, data, determinations and/or identifications obtained via the methods described herein to an individual, clinic, or healthcare professional, e.g., a clinician, a medical doctor. In other embodiments, a person identified as having an increased risk for coronary heart disease is administered a therapy to delay the onset, prevent the onset or slow the progression of coronary heart disease. In some embodiments, a person identified as having an increased risk for a myocardial infarction is administered a therapy to delay or prevent the onset of a myocardial infarction. In particular embodiments, a person characterized for increased risk for coronary atherosclerosis is treated with a therapy to delay the onset of or slow progression of the coronary atherosclerosis, particularly wherein the therapy comprises a lipid-lowering medication.

The invention provides reagents and kits for practicing the disclosed methods. In one embodiment, the invention provides a kit comprising one or more components for detecting the presence of an RA-CHR9 allele in a human subject.

3.1. Terminology

As used herein, reference to particular positions on human chromosome 9 are defined based on NCBI Build 36 coordinates (see, e.g., NCBI Accession Number NC_000009.10 and the following websites regarding the NCBI Build 36 coordinates: http://dec2007.archive.ensembl.org/Homo_sapiens/assemblies.html; and http://www.ncbi.nlm.nih.gov/mapview/stats/BuildStats.cgi?taxid-9606&build-36&ver=1) unless otherwise indicated.

As used herein, the terms "about" and "approximately", unless otherwise indicated, refer to a value that is no more than 10%, 8%, 5%, 2% or 1% above or below the value being modified by the term.

As used herein, the term "coronary heart disease" has its common meaning, for example, it refers to a disease caused by the narrowing of the small blood vessels that supply blood and oxygen to the heart and includes symptoms and events resulting therefrom, such as (without limitation) myocardial infarction, coronary atherosclerosis, angina, and congestive heart failure. In certain embodiments, the term "coronary heart disease" refers to myocardial infarction. In some embodiments, the term "coronary heart disease" refers to coronary atherosclerosis. In certain embodiments, the term "coronary heart disease" refers to the conditions of the humans enrolled in the Ottawa Heart Study, the Atherosclerosis Risk in Communities Study, The Copenhagen City Heart Study and/or the Dallas Heart Study As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human infant" refers to a newborn to 1 year old year human.

As used herein, the term "human toddler" refers to a human that is 1 year to 3 years old.

As used herein, the term "more frequently" in the context of an allele, haplotype or SNP means that a particular allele, haplotype or SNP is present at a statistically significantly higher frequency in a population of human subjects that have coronary heart disease relative to a population of human subjects that do not have coronary heart disease.

As used herein, the term "isolated" in the context of a nucleic acid (e.g., DNA, RNA, cDNA, etc.) refers to a nucleic acid that is substantially free of cellular material or contaminating nucleic acids from the cell or tissue source from which it is derived, or substantially free of chemical precursors or other chemicals when chemically synthesized. The phrase "substantially free of cellular material" includes preparations of a nucleic acid in which the nucleic acid is separated from cellular components of the cells from which it is isolated or produced. Thus, a nucleic acid that is substantially free of cellular material includes preparations of a nucleic acid having less than about 30%, 25%, 20%, 15%, 10%, or 5% (by dry weight) of a contaminating nucleic acid (e.g., a heterologous nucleic acid). When the nucleic acid is produced by chemical synthesis, it is preferably substantially free of chemical precursors or other chemicals, i.e., it is separated from chemical precursors or other chemicals which are involved in the synthesis of the nucleic acid. Accordingly, such preparations of a nucleic acid have less than about 30%, 20%, 10%, 5% (by dry weight) of chemical precursors or compounds other than the nucleic acid of interest. In a specific embodiment, a nucleic acid disclosed herein is isolated.

As used herein, the terms "person", "patient" and "subject" are used interchangeably and refer to a human.

4. BRIEF DESCRIPTION OF THE FIGURES

FIG. 1. Study design for identification and validation of sequence variants associated with coronary heart disease. Assuming independence, the probability of any single SNP achieving a nominal significance level of 0.025 in all three studies with the associations being in the same direction was $3.9 \times 10^{-6}$ ($0.025^3 \times 0.52$), thus none of the 100,000 SNPs would be expected by chance to replicate consistently in all three comparisons.

FIG. 2A. Fine mapping of the genomic interval on chromosome 9 associated with coronary heart disease. A. SNPs spaced ~5 kb apart in the interval extending 175 kb upstream and downstream of rs10757274 and rs2383206 were assayed in 500 cases and 500 controls from the Ottawa Heart Study population. Bars represent P values (determined using Chi-Square tests) for differences in allele frequency between cases and controls. Arrowheads indicate rs10757274 and rs2383206. The asterisk represents rs518394. The risk interval is indicated with a gray box. The linkage disequilibrium map indicates pairwise $r^2$ values. Blocks are shaded on a continuous scale where white represents an $r^2$ of 0 and black represents an $r^2$ of 1. FIG. 2B. Physical map of the region showing the location of the risk interval (gray box) relative to the noncoding RNA DQ485453 and adjacent genes: CDKN2A, ARF, and CDKN2B. Arrowheads indicate rs10757274 and rs2383206 and the asterisk represents rs518394 (see FIG. 2A).

5. DETAILED DESCRIPTION OF SPECIFIC EMBODIMENTS OF THE INVENTION

In one aspect, the invention provides a method for determining whether a person carries an allele associated with increased risk for coronary heart disease ("CHD"), the method comprising detecting whether the person has an RA-CHR9 allele. In one embodiment, the invention provides a method for determining whether a person carries an allele associated with increased risk for coronary heart disease, the method comprising detecting one, two, three or more, all or any combination of the single nucleotide polymorphisms (SNPs) found in an RA-CHR9 allele, such as those SNPs in Table 7, Table 8, Table 10 or Table 11. In specific embodiments, a human subject is identified as being homozygous for a RA-CHR9 allele. As demonstrated in the working example below, a human subject that is homozygous for a RA-CHR9 allele can exhibit a greater likelihood of developing coronary heart disease than a human subject that is heterozygous for the RA-CHR9 allele. In a specific embodiment, a human subject that is homozygous for a RA-CHR9 allele has at least a 5%, 10%, 15% or 25% or a 5% to 25%, 5% to 30%, or 10% to 25% greater likelihood of developing coronary heart disease than a human subject that is heterozygous for the RA-CHR9 allele. In other embodiments, a human subject is identified as being heterozygous for a RA-CHR9 allele. In particular embodiments, the person subject to evaluation has a family history of coronary atherosclerosis. In some embodiments, the person subject to evaluation has a family history of myocardial infarction.

In one embodiment, the invention provides a method for determining whether a person carries an allele associated with increased risk for coronary atherosclerosis, the method comprising detecting whether the person has an RA-CHR9 allele. In one embodiment, the invention provides a method for determining whether a person carries an allele associated with increased risk for coronary atherosclerosis, the method comprising the step of: determining whether the person has an RA-CHR9 allele, as detailed below. The RA-CHR9 allele may be detected by any suitable, specific technique known in the art, such as, for example, mass spectroscopy, oligonucleotide microarray analysis, allele-specific hybridization, allele-specific PCR, and sequencing. In a specific embodiment, the determining step comprises determining whether the person has an RA-CHR9 allele-associated single nucleotide polymorphism (SNP). Suitable SNPs are described below, and alternative suitable RA-CHR9 allele-associated SNPs are readily identified as described below. In particular embodiments, the determining step comprises determining whether the person has an RA-CHR9 allele-associated SNP selected from the group consisting of rs10757274 and rs2383206, rs6475606, rs1412832, rs10811645, and rs7865618.

In another embodiment, the invention provides a method for determining whether a human subject is at increased risk for coronary heart disease, comprising detecting whether a risk allele in an approximately 58 kb region extending from approximately position 22,062,301 to approximately position 22,120,389 of human chromosome 9 is present in a human subject, wherein the risk allele is more frequently present in a population of humans with coronary heart disease compared to a population of humans that do not have coronary heart disease, and wherein the presence of the risk allele indicates that the human subject has an increased risk for coronary heart disease. In some embodiments, the risk allele is in a region extending from position 22,062,301+/−5808, 5000, 4407, 4000, 3000, 2500, 2000, 1500, 1101, 1000, 550, 500, 250, 200, 150, 100 or 50 nucleotides to position 22,120,89+/−5808, 5000, 4407, 4000, 3000, 2500, 2000, 1500, 1000, 500, 250, 200, 150, 100 or 50 nucleotides of human chromosome 9. In a specific embodiment, the risk allele is in a region extending from position 22,062,301 to position 22,120,389 of human chromosome 9. In certain embodiments, the risk allele is at one or more of the positions identified in Table 7, Table 8, Table 10 or Table 11. In specific embodiments, a human subject is identified as being homozygous for a risk allele. As demonstrated in the working example below, a human subject that is homozygous for a risk allele can exhibit a greater likelihood of developing coronary heart disease than a human subject that is heterozygous for the risk allele. In a specific embodiment, a human subject that is homozygous for a risk allele is at least a 5%, 10%, 15% or 25%, or a 5% to 25%, 5% to 30% or 10% to 25% more likely to develop coronary heart disease than a human subject heterozygous for the risk allele. In other embodiments, a human subject is identified as being heterozygous for a risk allele.

In another aspect, the invention provides a method for determining whether a human subject is at increased risk for coronary heart disease, comprising detecting whether a human chromosome 9 haplotype comprising a guanine nucleotide at position 22086055 (rs10757274) and/or a guanine nucleotide at position 22105026 (rs2383206) is present in a human subject, wherein the presence of the haplotype indicates that the human subject has an increased risk for coronary heart disease. In specific embodiments, a human subject is identified as being homozygous for a haplotype. As demonstrated in the working example below, a human subject that is homozygous for a chromosome 9 haplotype can exhibit a greater likelihood of developing coronary heart disease than a human subject that is heterozygous for the haplotype. In a specific embodiment, a human subject that is homozygous for a chromosome 9 haplotype has at least a 5%, 10%, 15% or 25%, or a 5% to 25%, 5% to 30% or 10% to 25% greater likelihood of developing coronary heart disease than a human subject that is heterozygous for the haplotype. In other embodiments, a human subject is identified as being heterozygous for a chromosome 9 haplotype allele. In one embodiment, the haplotype comprises a guanine nucleotide at positions 22086055 (rs10757274) and 22105026 (rs2383206) of chromosome 9. In another embodiment, the haplotype comprises a guanine nucleotide at position 22078260 (rs10757274) and/or a guanine nucleotide at position 22105026 (rs2383206), and at least one, two, three, or more, all or any combination of the SNPs recited in Table 7, Table 8, Table 10 or Table 11. In a specific embodiment, the haplotype is in an approximately 58 kb region extending from about position 22062301 to about 22120389 of human chromosome 9. In certain embodiments, the haplotype is in a region extending from position 22,062,301+/−5808, 5000, 4407, 4000, 3000, 2500, 2000, 1500, 1101, 1000, 550, 500, 250, 200, 150, 100 or 50 nucleotides to position 22,120,389+/−5808, 4407, 4000, 3000, 2000, 1500, 1100, 1000, 550, 500, 250, 200, 150, 100 or 50 nucleotides of human chromosome 9.

In another aspect, the invention provides a method for determining whether a human subject is at increased risk for coronary heart disease, comprising detecting whether a polymorphism with a linkage disequilibrium of between 0.5 to 1, 0.5 to 0.90, or 0.5 to 0.80, or 0.5 to 0.75 with a risk allele in an approximately 58 kb region extending from about 22,062,301 to about 22,120,389 of human chromosome 9 is present in a human subject, wherein the presence of the polymorphism indicates that the human subject has an increased risk for coronary heart disease. In some embodiments, the haplotype is in a region extending from position 22,062,301+/−5808, 5000, 4407, 4000, 3000, 2500, 2000, 1500, 1101, 1000, 550, 500, 250, 200, 150, 100 or 50 nucleotides to position 22,120,389+/−5808, 4407, 4000, 3000, 2000, 1500, 1100, 1000, 550, 500, 250, 200, 150, 100 or 50 nucleotides of human chromosome 9. In a specific embodiment, the risk allele is in a region extending from position 22,062,301 to 22,120,389 of human chromosome 9. In specific embodiments, a human subject is identified as being homozygous for a polymorphism. As demonstrated in the working example below, a human subject that is homozygous for a polymorphism can exhibit a greater likelihood of developing coronary heart disease than a human subject that is heterozygous for the polymorphism. In a specific embodiment, a human subject that is homozygous for the haplotype has at least a 5%, 10%, 15% or 25% or a 5% to 25%, 5% to 30%, or 10% to 25% greater likelihood of developing coronary heart disease that a human subject that is heterozygous for the haplotype. In other embodiments, a human subject is identified as being heterozygous for a polymorphism.

In another aspect, the invention provides a method for determining whether a person carries an allele associated with increased risk for coronary heart disease (e.g., coronary atherosclerosis or myocardial infarction), comprising detecting whether a person carries at least one, two, three, four or more, all or any combination of the following SNPs, insertions, and/or deletions listed in Table 7, Table 8, Table 10 and/or Table 11, wherein the presence of at least one, two, three, four or more, all or any combination of the SNPs indicates that the human subject is at increased risk for coronary heart disease. In specific embodiments, a human subject is identified as being homozygous for a SNP(s). As demonstrated in the working example below, a human subject that is homozygous for a SNP(s) can exhibit a greater likelihood (e.g., at least a 5%, 10%, 15% or 25% or a 5% to 25%, 5% to 30%, or 10% to 25% higher likelihood) of developing coronary heart disease than a human subject that is heterozygous for the SNP(s). In other embodiments, a human subject is identified as being heterozygous for a SNP(s).

In certain embodiments, embodiments, the methods further comprise providing results, information, data, determinations and/or identifications obtained via the methods described herein to an individual, clinic, or healthcare professional, e.g., a clinician, a medical doctor. In other embodiments, a person identified as having an increased risk for coronary heart disease is administered a therapy to delay the onset, prevent the onset or slow the progression of coronary heart disease. In some embodiments, a person identified as having an increased risk for a myocardial infarction is administered a therapy to delay or prevent the onset of a myocardial infarction. In particular embodiments, a person characterized for increased risk for coronary atherosclerosis is treated with a therapy to delay onset of or slow progression of the coronary atherosclerosis, particularly wherein the therapy comprises a lipid-lowering medication.

The invention further provides reagents and kits for practicing the disclosed methods.

5.1. Methods for Detecting Increased Risk of Coronary Heart Disease

In one aspect, the invention provides a method for determining whether a human subject has an allele associated with increased-risk for coronary heart disease (e.g., coronary atherosclerosis or myocardial infarction), the method comprising detecting whether RA-CHR9 allele is present in a human subject. In some embodiments, the human subject is identified as having or determined to have an increased risk for coronary heart disease if the RA-CHR9 allele is detected. In some embodiments, the RA-CHR9 allele is approximately 58 kb and extends from about 22,062,301 to about 22,120,389 of human chromosome 9. In certain embodiments, the RA-CHR9 allele extends from position 22,062, 301+/−5508, 4407, 4000, 3000, 2500, 2000, 1500, 1101, 1000, 550, 500, 250, 200, 150, 100 or 50 nucleotides to position 22,120,389+/−5508, 4407, 4000, 3000, 2000, 1500, 1100, 1000, 550, 500, 250, 200, 150, 100 or 50 nucleotides of human chromosome 9. In some embodiments, the RA-CHR9 allele extends from position 22,062,040 to position 22,120,389 of human chromosome 9. In some embodiments, the RA-CHR9 allele extends from position 22,062,040 to position 22,120,389 of human chromosome 9. In some embodiments, the human subject is homozygous for the RA-CHR9 allele. In other embodiments, the human subject is heterozygous for the RA-CHR9 allele. The presence of an RA-CHR9 allele in a human subject can be detected in an in vitro assay, e.g., a nucleic acid sample (see Section 5.3 below) and techniques known to one of skill in the art or described in Section 5.4 below.

In certain embodiments, in addition to detecting the presence of an RA-CHR9 allele, one or more polymorphisms identified as being associated with an increased likelihood of coronary heart disease, such as those described in International Publication Nos. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2005/0112611, 2007/0031847, 2006/0228715, 2007/0072821, 2006/0223093, and 2005/0272054 (each of which are incorporated herein by reference) is also detected.

In one embodiment, the invention provides a method for determining whether a human subject has an allele associated with increased risk for coronary heart disease (e.g., coronary atherosclerosis or myocardial infarction), the method comprising detecting whether one, two, three or more, all or any combination of the SNPs, insertions and/or deletions found in an RA-CHR9 allele, such as those SNPs, insertions and/or deletions in Table 7, Table 8, Table 10 or Table 11, are present, wherein the detection of such SNPs insertions and/or deletions indicates that the human subject has an allele associated with coronary heart disease. In some embodiments, the human subject is identified as having or determined to have an increased risk for coronary heart disease if such an allele is detected. The presence of said one, two, three or more or all of the SNPs, insertions and/or deletions found in an RA-CHR9 allele in a human subject can be detected in an in vitro assay, e.g., a nucleic acid sample (see Section 5.3 below) and techniques known to one of skill in the art or described in Section 5.4 below. Non-limiting examples of SNPs, insertions, and deletions found in an RA-CHR9 allele include: the SNP found at position 22062264; the SNP found at position 22062301; the SNP found at position 22062638; the SNP at position 22067543; the SNP found at position 22062719; the SNP found at position 22071397; the SNP found at position 22071850; the SNP found at position 22078090; the SNP found at position 22078094; the SNP found at position 22078260; the deletion found at position 22078465; the SNP found at position 22086055; the SNP found at position 22088574; the SNP found at position 22088619; the insertion found at position 22089755; the SNP found at position 22090176; the SNP found at position 22091702; the SNP found at position 22092165; the SNP found at position 22093183; the SNP found at position 22093341; the SNP found at position 22093813; the SNP found at position 22095927; the SNP found at position 22096731; the SNP found at position 22100131; the insertion found at position 22101587; the SNP found at position 22102241; the SNP found at position 22102427; the SNP found at position 22104469; the SNP found at position 22104495; the SNP found at position 22105026; the SNP found at position 22105286; the SNP found at position 22106046; the SNP found at position 22106220; the insertion found at position 22110491; the SNP found at position 22113766; the SNP found at position 22114123; the SNP found at position 22114140; the SNP found at position 22115347; and the SNP found at position 22115503. In some embodiments, the human subject is homozygous for a SNP. In other embodiments, the human subject is heterozygous for a SNP.

In another aspect, the invention provides a method for determining whether a human subject carries an allele associated with an increased risk for coronary heart disease (e.g., coronary atherosclerosis or myocardial infarction), comprising detecting whether one, two, three, four or more risk alleles in an approximately 58 kb region extending from about 22,062,301 to about 22,120,389 of human chromosome 9 that are more frequently present in a population of humans with coronary heart disease compared to a population of humans that do not have coronary heart disease are present in a human subject. In some embodiments, the human subject is identified as having or determined to have an increased risk for coronary heart disease if such an allele is detected. In some embodiments, the risk allele is in an approximately 58 kb region extending from about position 22,062,301 to about position 22,120,389 of human chromosome 9. In some embodiments, the risk allele is in a region extending from position 22,062,301+/−5808, 5000, 4407, 4000, 3000, 2500, 2000, 1500, 1101, 1000, 550, 500, 250, 200, 150, 100 or 50 nucleotides to position 22,120,389+/− 5808, 5000, 4407, 4000, 3000, 2500, 2000, 1500, 1101, 1000, 550, 500, 250, 200, 150, 100 or 50 nucleotides of human chromosome 9. In a specific embodiment, the risk allele is in a region extending from position 22,062,301 to 22,120,389 of human chromosome 9. In some embodiments, the human subject is homozygous for the risk allele. In other embodiments, the human subject is heterozygous for the risk allele. The presence of one, two, three, four or more of the risk alleles can be detected using an in vitro assay, e.g., a nucleic acid sample (see Section 5.3 below) and techniques known to one of skill in the art or described in Section 5.4 below.

In certain embodiments, one, two, three, four or more of the risk alleles is/are at one, two, three, four or more positions identified in Table 7, Table 8, Table 10 or Table 11. In one embodiment, one, two, three, four or more of the risk alleles is at one, two, three, four or more of the following positions of human chromosome 9: position 22062264; position 22062301; position 22062638; position 22067543; position 22062719; position 22071397; position 22071850; position 22078090; position 22078094; position 22078260; position 22086055; position 22088574; position 22088619; position 22078465; position 22089755; position 22090176; position 22091702; position 22092165; position 22093183; position 22093341; position 22093813; position 22095927; position 22096731; position 22100131; position 22101587; position 22102241; position 22102427; position 22104469; position 22104495; position 22105026; position 22105286; position 22106046; position 22106220; position 22110491; position 22113766; position 22114123; position 22114140; position 22115347; and/or position 22115503. In another embodiment, one, two, three, four or more of the risk alleles is at one, two, three, four or more of the following: rs9632884, rs6475606, rs10757272, rs10757274, rs4977574, rs2891168, rs1333042, rs2383206, rs1333048, or rs1333049. In a specific embodiment, at least one or two of the risk alleles is at rs10757274 and/or rs2383206.

In certain embodiments, in addition to detecting risk alleles in an approximately 58 kb region extending from about 22,062,301 to about 22,120,389 of chromosome 9, one or more polymorphisms identified as being associated with an increased likelihood of coronary heart disease, such as those described in International Publication Nos. WO 2007/006862, WO 2004/03576, WO 20041035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/ 0280917, 2006/0019269, 2005/0282855, 2005/0164220, 2005/0113408, 2005/0112611, 2007/0031847, 2006/ 0228715, 2007/0072821, 2006/0223093, and 2005/0272054 (each of which are incorporated by herein by reference) is also detected. In a specific embodiment, the presence of one, two or more risk alleles indicates that the human subject has a 10% to 25%, 10% to 20%, 10% to 15%, 12.5% to 15%, 10% to 30%, 10% to 40% or 10% to 50% increased risk for coronary heart disease.

In another aspect, the invention provides a method for determining whether a human subject carries a haplotype associated with increased risk for coronary heart disease (e.g., coronary atherosclerosis or myocardial infarction), comprising detecting whether a human chromosome 9 haplotype comprising a guanine nucleotide at position 220086055 (rs10757274) and/or a guanine nucleotide at position 22105026 (rs2383206) is present in a human subject. In some embodiments, the human subject is identified as having or determined to have an increased risk for coronary heart disease if the haplotype is detected. In some embodiments, the human subject is homozygous for the haplotype. In other embodiments, the human subject is heterozygous for the haplotype. The presence of the haplotype in a human subject can be detected using an in vitro assay, e.g., a nucleic acid sample (see Section 5.3 below) and techniques known to one of skill in the art or described in Section 5.4 below. In a specific embodiment, the presence of the haplotype indicates that the human subject has a 10% to 25%, 10% to 20%, 10% to 15%, 12.5% to 15%, 10% to 30%, 10% to 40% or 10% to 50% increased risk for coronary heart disease. In one embodiment, the haplotype comprises a guanine nucleotide at positions 22086055 (rs10757274) and 22105026 (rs2383206) of human chromosome 9. In another embodiment, the haplotype comprises a guanine nucleotide at position 220086055 (rs10757274) and/or a guanine nucleotide at position 22105026 (rs2383206) on human chromosome 9, and at least one, two, three, or more, all or any combination of the following SNPs on human chromosome 9: a cytosine nucleotide at position 22062301 (rs9632884), a thymine nucleotide at position 22071850 (rs6475606), a thymine nucleotide at position 22078260 (rs10757272), a guanine at position 22088574 (rs4977574), a guanine nucleotide at position 22088619 (rs2891168), a guanine nucleotide at position 22093813 (rs1333042), a cytosine nucleotide at position 22115347 (rs1333048), and/or a cytosine nucleotide at position 22115503 (rs1333049). In another embodiment, the haplotype comprises a guanine nucleotide at position 22086055 (rs1075724) and/or a guanine nucleotide at position 22105026 (rs283206) and at least one, two, three or more or all of the following on human chromosome 9: a guanine nucleotide at position 22062264; a cytosine nucleotide at position 22062301; an adenine nucleotide at position 22062638; a guanine nucleotide at position 22062719; a thymine nucleotide at position 22071397; a thymine nucleotide position 22071850; an thymine nucleotide position 22078090; a guanine nucleotide at position 22078094; a thymine nucleotide position 22078260; a deletion at position 22078465; a guanine nucleotide at position 22088574; a guanine nucleotide at position 22088619; an insertion at position 22089755; a cytosine nucleotide position 22090176; a cytosine nucleotide at position 22091702; a thymine nucleotide at position 22092165; a thymine nucleotide at position 22093183; a guanine nucleotide at position 22093341; a guanine nucleotide at position 22093813; a cytosine nucleotide at position 22095927; an adenine nucleotide at position 22096731; a cytosine nucleotide at position 22100131; an insertion at position 22101587; a cytosine nucleotide at position 22102241; a guanine nucleotide at position 22102427; a cytosine nucleotide at position 22104469; a guanine nucleotide at position 22104495; a cytosine nucleotide at position 22105286; a guanine nucleotide at position 22106046; a cytosine nucleotide at position 22106220; an insertion at position 22110491; a cytosine nucleotide at position 22113766; an adenine nucleotide at position 22114123; a thymine nucleotide at position 22114140; a cytosine nucleotide at position 22115347; and/or a cytosine at position 22115503. In some embodiments, the haplotype is in an approximately 58 kb region extending from about position 22,062,301 to about 22,120,389 of human chromosome 9. In certain embodiments, the haplotype is in a region extending from position 22,062,301+/−5808, 5000, 4407, 4000, 3000, 2500, 2000, 1500, 1101, 1000, 550, 500, 250, 200, 150, 100 or 50 nucleotides to position 22,120,398+/−5808, 5000, 4407, 4000, 3000, 2500, 2000, 1500, 1101, 1000, 550, 500, 250, 200, 150, 100 or 50 nucleotides of human chromosome 9. In a specific embodiment, the haplotype is in a region extending from position 22062301 to 22120389 of human chromosome 9.

In certain embodiments, in addition to detecting a human chromosome 9 haplotype comprising a guanine nucleotide at position 22086055 (rs10757274) and/or 22105026 (rs2383206), one or more polymorphisms identified as being associated with an increased likelihood of coronary heart disease, such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2005/0112611, 2007/0031847, 2006/0228715, 2007/0072821, 2006/0223093, and 2005/0272054 (each of which are incorporated by herein by reference) is also detected.

In another aspect, the invention provides a method for determining whether a human subject has allele associated with increased risk for coronary heart disease (e.g., coronary atherosclerosis or myocardial infarction), comprising detecting whether a polymorphism with a linkage disequilibrium of between 0.5 to 1, 0.5 to 0.90, 0.5 to 0.80, 0.5 to 0.75, 0.75 to 1, or 0.85 to 1 with a risk allele in an approximately 58 kb region extending from about 22,062,301 to about 22,120,389 of chromosome 9 is present in a human subject. In some embodiments, the human subject is determined to have or identified as having an increased risk for coronary heart disease if the polymorphism is detected. In some embodiments, the human subject is homozygous for the polymorphism. In other embodiments, the human subject is heterozygous for the polymorphism. In certain embodiments, the presence of a polymorphism with a linkage disequilibrium of at least $r^2$=0.50, 0.55, 0.60, 0.65, 0.70, 0.75, 0.80 or 0.85 with a risk allele in an approximately 58 kb region extending from about 22,062,301 to about 22,120,389 of human chromosome 9 in a human subject is detected. In some embodiments, a polymorphism with a linkage disequilibrium of at least $r^2$=0.89, 0.90, 0.91, 0.92, 0.93, 0.94 0.95, 0.96, 0.97, 0.98 or 0.99 with a risk allele in an approximately 58 kb region extending from about 22,062,301 to about 22,120,389 of human chromosome 9 in a human subject is detected. In a specific embodiment, a polymorphism with a linkage disequilibrium of $r^2$=0.89, 0.90, 0.91, 0.92, 0.93, 0.94 0.95, 0.96, 0.97, 0.98, 0.99 or 1 with a risk allele in an approximately 58 kb region extending from about 22,062,301 to about 22,120,389 of human chromosome 9 in a human subject is detected. In some embodiments, the risk allele is in a region extending from position 22,062,301+/−5808, 5000, 4407, 4000, 3000, 2500, 2000, 1500, 1101, 1000, 550, 500, 250, 200, 150, 100 or 50 nucleotides to position 22,120,3889+/−5808, 5000, 4407, 4000, 3000, 2500, 2000, 1500, 1101, 1000, 550, 500, 250, 200, 150, 100 or 50 nucleotides of human chromosome 9. In a specific embodiment, the risk allele is in a region extending from position 22,062,301 to position 22,120,389 of human chromosome 9.

In one embodiment, the risk allele is a SNP, insertion or deletion listed in Table 7, Table 8, Table 10 or Table 11. In one embodiment, the risk allele is at rs10757274 or rs2383206. In another embodiment, the risk allele is at rs9632884, rs6475606, rs10757272, rs10757274, rs4977574, rs2891168, rs1333042, rs2383206, rs1333048 or rs1333049. The presence of the polymorphism in the human subject can be detected using an in vitro assay, e.g., a nucleic acid sample (see Section 5.3 below) and techniques known to one of skill in the art or described in Section 5.4 below. In a specific embodiment, the presence of the polymorphism indicates that the human subject has a 10% to 25%, 10% to 20%, 10% to 15%, 12.5% to 15%, 10% to 30%, 10% to 40% or 10% to 50% increased risk for coronary heart disease.

In certain embodiments, in addition to detecting a polymorphism in an approximately 58 kb region extending from about 22,062,301 to about 22,120,389 of human chromosome 9 with a linkage disequilibrium of at least $r^2$=0.5, 0.55, 0.65, 0.70. 0.75, 0.85, 0.89, 0.90, 0.95 or 1, one or more polymorphisms identified as being associated with an increased likelihood of coronary heart disease, such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2005/0112611, 2007/0031847, 2006/0228715, 2007/0072821, 2006/0223093, and 2005/0272054 (each of which are incorporated by herein by reference) is also detected.

Techniques for determining whether a polymorphism is in linkage disequilibrium with a risk allele are well-known to the one of skill in the art. See. e.g., the following for information concerning linkage disequilibrium in the human genome: Wall et al., "Haplotype blocks and linkage disequilibrium in the human genome", Nat Rev Genet. 2003 August; 4(8):587-97; Garner et al., "On selecting markers for association studies: patterns of linkage disequilibrium between two and three diallelic loci", Genet Epidemiol. 2003 January; 24(1):57-67; Ardlie et al., "Patterns of linkage disequilibrium in the human genome", Nat Rev Genet. 2002 April; 3(4):299-309 (erratum in Nat Rev Genet 2002 July; 3(7):566); and Remm et al., "High-density genotyping and linkage disequilibrium in the human genome using chromosome 22 as a model"; Curr Opin Chem Biol. 2002 February; 6(1):24-30; Haldane J B S (1919) The combination of linkage values, and the calculation of distances between the loci of linked factors. J Genet 8:299-309; Mendel, G. (1866) Versuche uber Pflanzen-Hybriden. Verhandlungen des naturforschenden Vereines in Brunn [Proceedings of the Natural History Society of Brunn]; Lewin B (1990) Genes IV Oxford University Press, New York, USA; Hartl D L and Clark A G (1989) Principles of Population Genetics 2.sup.nd ed. Sinauer Associates, Inc. Sunderland, Mass., USA; Gillespie J H (2004) Population Genetics: A Concise Guide. 2.sup.nd ed. Johns Hopkins University Press. USA; Lewontin R C (1964) The interaction of selection and linkage. 1. General considerations; heterotic models. Genetics 49:49-67; Hoel P G (1954) Introduction to Mathematical Statistics 2.sup.nd ed. John Wiley & Sons, Inc. New York, USA; Hudson R R (2001) Two-locus sampling distributions and their application. Genetics 159:1805-1817; Dempster A P, Laird N M, Rubin D B (1977) Maximum likelihood from incomplete data via the EM algorithm. J R Stat Soc 39:1-38; Excoffier L, Slatkin M (1995) Maximum-likelihood estimation of molecular haplotype frequencies in a diploid population. Mol Biol Evol 12(5):921-927; Tregouet D A, Escolano S, Tiret L, Mallet A, Golmard J L (2004) A new algorithm for haplotype-based association analysis: the Stochastic-EM algorithm. Ann Hum Genet 68(Pt 2):165-177; Long A D and Langley C H (1999) The power of association studies to detect the contribution of candidate genetic loci to variation in complex traits. Genome Research 9:720-731; Agresti A (1990) Categorical Data Analysis. John Wiley & Sons, Inc. New York, USA; Lange K (1997) Mathematical and Statistical Methods for Genetic Analysis. Springer-Verlag New York, Inc. New York, USA; The International HapMap Consortium (2003) The International HapMap Project. Nature 426:789-796; The International HapMap Consortium (2005) A haplotype map of the human genome. Nature 437:1299-1320; Thorisson G A, Smith A V, Krishnan L, Stein L D (2005), The International HapMap Project Web Site. Genome Research 15:1591-1593; McVean G, Spencer C C A, Chaix R (2005) Perspectives on human genetic variation from the HapMap project. PLoS Genetics 1(4): 413-418; Hirschhorn J N, Daly M J (2005) Genome-wide association studies for common diseases and complex traits. Nat Genet 6:95-108; Schrodi S J (2005) A probabilistic approach to large-scale association scans: a semi-Bayesian method to detect disease-predisposing alleles. SAGMB 4(1):3 1; Wang W Y S, Barratt B J, Clayton D G, Todd J A (2005) Genome-wide association studies: theoretical and practical concerns. Nat Rev Genet 6:109-118. Pritchard J K, Przeworski M (2001) Linkage disequilibrium in humans: models and data. Am J Hum Genet 69:1-14. The parameter $r^2$ is commonly used in the genetics art to characterize the extent of linkage disqulibirium between two genetic loci (see. e.g., Hudson et al. (2001) Genetics 159:1805-1817).

In another aspect, the invention provides a method for determining whether a human subject carries a SNP, insertion and/or deletion associated with an increased risk for coronary heart disease (e.g., coronary atherosclerosis or myocardial infarction), comprising detecting the whether at least one, two, three, four or more or all of the SNPs, insertions and/or deletions listed in Table 7, Table 8, Table 10 or Table 11 is present in the human subject. In some embodiments, the human subject is identified as having or determined to have an increased risk for developing coronary heart disease if the SNP(s), insertion(s) and/or deletion(s) is/are detected. In a specific embodiment, the presence of one, two, three four or more or all SNPs, insertions and/or deletions listed in Table 7, Table 8, Table 10 or Table 11 indicates that the human subject has a 10% to 25%, 10% to 20%, 10% to 15%, 12.5% to 15%, 10% to 30%, 10% to 40% or 10% to 50% increased risk for coronary heart disease. In some embodiments, the human subject is homozygous for a SNP(s). In certain embodiments, the human subject that is homozygous for the SNP(s) has a 10% to 30%, 10% to 25% or 10 to 20% greater likelihood of developing coronary heart disease than a human subject that is heterozygous for the SNP(s). In other embodiments, the human subject is heterozygous for a SNP(s). The presence of the allele in a human subject can be detected using an in vitro assay, e.g., a nucleic acid sample (see Section 5.3 below) and techniques known to one of skill in the art or described in Section 5.4 below.

In another embodiment, the invention provides a method for determining whether a human subject carries a SNP, insertion and/or deletion associated with an increased risk for having a myocardial infarction, comprising detecting the whether at least one, two, three, four or more or all of the SNPs, insertions and/or deletions listed in Table 7, Table 8, Table 10 or Table 11 is present in the human subject. In some embodiments, the human subject is identified as having or determined to have an increased risk for having a myocardial infarction if one, two, three four or more, all or any combination the SNPs, insertions and/or deletions is/are detected. In a specific embodiment, the presence of one, two, three four or more, all or any combination of the SNPs, insertions and/or deletions listed in Table 7, Table 8, Table 10 or Table 11 indicates that the human subject has a 10% to 25%, 10% to 20%, 10% to 15%, 12.5% to 15%, 10% to 30%, 10% to 40% or 10% to 50% increased risk for having a myocardial infarction. In some embodiments, the human subject is homozygous for a SNP(s). In certain embodiments, the human subject that is homozygous for the SNP(s) has a 10% to 30%, 10% to 25% or 10% to 20% greater likelihood of having a myocardial infarction than a human subject that is heterozygous for the SNP(s). In other embodiments, the human subject is heterozygous for a SNP(s).

In certain embodiments, in addition to detecting one or more SNPs, insertions and/or deletions listed in Table 7, Table 8, Table 10 or Table 11, one or more polymorphisms identified as being associated with an increased likelihood of coronary heart disease (e.g., coronary atherosclerosis or myocardial infarction), such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2005/0112611, 2007/0031847, 2006/0228715, 2006/0223093, 2007/0072821 and 2005/0272054 (each of which are incorporated by herein by reference) is also detected.

In one embodiment, the invention provides a method for determining whether a human subject carries a SNP, insertion and/or deletion associated with increased risk for coronary heart disease (e.g., coronary atherosclerosis or myocardial infarction), comprising detecting whether at least one, two, three, four or more, all or any combination of the following SNPs, insertions and/or deletions on human chromosome 9 are present in the human subject: a guanine nucleotide at position 22062264; a cytosine nucleotide at position 22062301; an adenine nucleotide at position 22062638; a guanine nucleotide at position 22062719; a thymine nucleotide at position 22071397; a thymine nucleotide position 22071850; a thymine nucleotide position 22078090; a guanine nucleotide at position 22078094; a thymine nucleotide position 22078260; a deletion at position 22078465; a guanine nucleotide at position 22086055; a guanine nucleotide at position 22088574; a guanine nucleotide at position 22088619; an insertion at position 22089755; a cytosine nucleotide position 22090176; a cytosine nucleotide at position 22091702; a thymine nucleotide at position 22092165; a thymine nucleotide at position 22093183; a guanine nucleotide at position 22093341; a guanine nucleotide at position 22093813; a cytosine nucleotide at position 22095927; an adenine nucleotide at position 22096731; a cytosine nucleotide at position 22100131; an insertion at position 22101587; a cytosine nucleotide at position 22102241; a guanine nucleotide at position 22102427; a cytosine nucleotide at position 22104469; a guanine nucleotide at position 22104495; a guanine nucleotide at 22105026; a cytosine nucleotide at position 22105286; a guanine nucleotide at position 22106046; a cytosine nucleotide at position 22106220; an insertion at position 22110491; a cytosine nucleotide at position 22113766; an adenine nucleotide at position 22114123; a thymine nucleotide at position 22114140; a cytosine nucleotide at position 22115347; and/or a cytosine at position 22115503. In some embodiments, the human subject is identified as having or determined to have an increased risk for coronary heart disease if one, two, three four or more, all or any combination the SNPs, insertions and/or deletions is/are detected. In a specific embodiment, the human subject is has an increased risk for coronary heart disease. In a specific embodiment, the presence of one, two, three four or more, all or any combination of the SNPs, insertions and/or deletions listed in Table 7, Table 8, Table 10 or Table 11 indicates that the human subject has a 10% to 25%, 10% to 20%, 10% to 15%, 12.5% to 15%, 10% to 30%, 10% to 40% or 10% to 50% increased risk for having a myocardial infarction. In some embodiments, the human subject is homozygous for a SNP(s). In certain embodiments, the human subject that is homozygous for the SNP(s) has a 10% to 30%, 10% to 25% or 10% to 20% greater likelihood for developing coronary heart disease than a human subject that is heterozygous for the SNP(s). In other embodiments, the human subject is heterozygous for a SNP(s). The presence of SNPs in a human subject can be detected using an in vitro assay, e.g., a nucleic acid sample (see Section 5.3 below) and techniques known to one of skill in the art or described in Section 5.4 below.

In another embodiment, the invention provides a method for determining whether a human subject has a SNP associated with an increased risk for coronary heart disease (e.g., coronary atherosclerosis or myocardial infarction), comprising detecting whether a guanine nucleotide at position 22086055 (rs10757274) and/or a guanine nucleotide at position 22105026 (rs2383206) of human chromosome 9 is/are present in the human, and at least one, two, three, or more, all or any combination of the following SNPs on human chromosome 9: a cytosine nucleotide at position 22062301 (rs9632884), a thymine nucleotide at position 22071850 (rs6475606), a thymine nucleotide at position 22078260 (rs10757272), a guanine at position 22088574 (rs4977574), a guanine nucleotide at position 22088619 (rs2891168), a guanine nucleotide at position 22093813 (rs1333042), a cytosine nucleotide at position 22115347 (rs1333048), and/or a cytosine nucleotide at position 22115503 (rs1333049). In a specific embodiment, the human subject is has an increased risk of myocardial infarction. In some embodiments, the human subject is identified as having or determined to have an increased risk for having a coronary heart disease if two, three four or more, all or any combination the SNPs are detected. In a specific embodiment, the presence of two, three four or more, all or any combination of the SNPs listed in Table 7, Table 8, Table 10 or Table 11 indicates that the human subject has a 10% to 25%, 10% to 20%, 10% to 15%, 12.5% to 15/%, 10% to 30%, 10% to 40% or 10% to 50% increased risk for having a myocardial infarction. In some embodiments, the human subject is homozygous for a SNP(s). In certain embodiments, the human subject that is homozygous for the SNP(s) has a 10% to 30%, 10% to 25% or 10% to 20% greater likelihood of having a myocardial infarction than a human subject that is heterozygous for the SNP(s). In other embodiments, the human subject is heterozygous for a SNP(s). The presence of SNPs in a human subject can be detected using an in vitro assay, e.g., a nucleic acid sample (see Section 5.3 below) and techniques known to one of skill in the art or described in Section 5.4 below.

In another embodiment, the invention provides a method for determining whether a human subject has a SNP associated with increased risk for coronary heart disease (e.g., coronary atherosclerosis or myocardial infarction), comprising detecting whether a guanine at position 22086055 (rs10757274) and a guanine at position 22105026 (rs2383206) of human chromosome 9 is present in the human subject. In some embodiments, the human subject is identified as having or determined to have an increased risk for developing coronary heart disease if the SNPs are detected. In a specific embodiment, the human subject is has an increased risk of myocardial infarction. In some embodiments, the human subject that is homozygous at positions 22086055 and 22105026 (i.e., has two guanine alleles at those positions) has a greater likelihood for developing coronary heart disease than a human subject heterozygous at those positions. In other embodiments, the human subject is heterozygous at position 22086055 and/or at position 22105026 of chromosome 9.

In another embodiment, the invention provides a method for determining whether a human subject has a SNP associated with increased risk for coronary heart disease (e.g., coronary atherosclerosis or myocardial infarction), comprising detecting whether a cytosine at position 22115503 (rs1333049) of human chromosome 9 is present in the human subject. In some embodiments, the human subject is identified as having or determined to have an increased risk for developing coronary heart disease if the SNP is detected. In a specific embodiment, the human subject is has an increased risk of myocardial infarction. In some embodiments, the human subject that is homozygous at positions 22115503 (rs1333049) (i.e., has two cytosine nucleotides at position 22115503 (rs1333049)) has a greater likelihood for developing coronary heart disease than a human subject heterozygous at that position 22115503 (rs1333049) of human chromosome 9. In other embodiments, the human subject is heterozygous at position 22115503 (rs1333049) of human chromosome 9.

In another embodiment, the invention provides a method for determining whether a human subject has a SNP associated with increased risk for coronary heart disease (e.g., coronary atherosclerosis or myocardial infarction), comprising detecting whether a guanine at position 22114477 (rs10757278) of human chromosome 9 is present in the human subject. In some embodiments, the human subject is identified as having or determined to have an increased risk for developing coronary heart disease if the SNP is detected. In a specific embodiment, the human subject is has an increased risk of myocardial infarction. In some embodiments, the human subject that is homozygous at positions 22114477 (rs10757278) (i.e., has two guanine nucleotides at position 22114477 (rs1075728) has a greater likelihood for developing coronary heart disease than a human subject heterozygous at position 22114477 (rs10757278) of human chromosome 9. In other embodiments, the human subject is heterozygous at position 22114477 (rs10757278) of human chromosome 9.

In another embodiment, the invention provides a method for determining whether a human subject has a SNP associated with increased risk for coronary heart disease (e.g., coronary atherosclerosis or myocardial infarction), comprising detecting whether a cytosine at position 22114477 (rs1333049) and a guanine at position 22114477 (rs10757278) of human chromosome 9 are present in the human subject. In some embodiments, the human subject is identified as having or determined to have an increased risk for developing coronary heart disease if the SNPs are detected. In a specific embodiment, the human subject is has an increased risk of myocardial infarction. In some embodiments, the human subject that is homozygous at position 22114477 (rs1333049) (i.e., two cytosine nucleotides at rs1333049) and homozygous at position 22114477 (rs10757278) (i.e., two guanine nucleotides at rs10757278) has a greater likelihood for developing coronary heart disease than a human subject heterozygous at position 22114477 (rs1333049) and at position 22114477 (rs10757278) of human chromosome 9. In other embodiments, the human subject is heterozygous at position 22114477 (rs1333049) and/or at position 22114477 (rs10757278) of human chromosome 9.

In one embodiment, the invention provides a method for determining whether a human subject has an increased risk for coronary heart disease (e.g., coronary atherosclerosis or myocardial infarction), comprising detecting whether at least one, two, three, four or more or all of the SNPs, insertions and/or deletions listed in Table 7, Table 8, Table 10 or Table 11 is present in a human subject, wherein the presence of one, two, three, four or more or all of the SNPs, insertions and/or deletions indicates that the human subject has an increased risk for coronary heart disease. In a specific embodiment, the human subject is has an increased risk of myocardial infarction. The presence of SNPs, insertions and/or deletions in a human subject can be detected using an in vitro assay, e.g., a nucleic acid sample (see Section 5.3 below) and techniques known to one of skill in the art or described in Section 5.4 below. In a specific embodiment, the presence of one, two, three four or more or all SNPs, insertions and/or deletions listed in Table 7, Table 8, Table 10 or Table 11 indicates that the human subject has a 10% to 25%, 10% to 20%, 10% to 15%, 12.5% to 15%, 10% to 30%, 10% to 40% or 10% to 50% increased risk for coronary heart disease.

In certain embodiments, in addition to detecting one or more SNPs, insertions and/or deletions listed in Table 7, Table 8, Table 10 or Table 11, one or more polymorphisms identified as being associated with an increased likelihood of coronary heart disease, such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 200510112611, 2007/0031847, 2006/0228715, 2006/0223093, 2007/0072821 and 2005/0272054 (each of which are incorporated by herein by reference) is also detected.

In one embodiment, the invention provides a method for determining whether a human subject has an increased risk for coronary heart disease (e.g., coronary atherosclerosis or myocardial infarction), comprising detecting whether at least one, two, three, four or more, all or any combination of the following SNPs, insertions and/or deletions on human chromosome 9 is/are present in a human subject: a guanine nucleotide at position 22062264; a cytosine nucleotide at position 22062301; an adenine nucleotide at position 22062638; a guanine nucleotide at position 22062719; a thymine nucleotide at position 22071397; a thymine nucleotide position 22071850; a thymine nucleotide position 22078090; a guanine nucleotide at position 22078094; a thymine nucleotide position 22078260; a deletion at position 22078465; a guanine nucleotide at position 22086055; a guanine nucleotide at position 22088574; a guanine nucleotide at position 22088619; an insertion at position 22089755; a cytosine nucleotide position 22090176; a cytosine nucleotide at position 22091702; a thymine nucleotide at position 22092165; a thymine nucleotide at position 22093183; a guanine nucleotide at position 22093341; a guanine nucleotide at position 22093813; a cytosine nucleotide at position 22095927; an adenine nucleotide at position 22096731; a cytosine nucleotide at position 22100131; an insertion at position 22101587; a cytosine nucleotide at position 22102241; a guanine nucleotide at position 22102427; a cytosine nucleotide at position 22104469; a guanine nucleotide at position 22104495; a guanine nucleotide at 22105026; a cytosine nucleotide at position 22105286; a guanine nucleotide at position 22106046; a cytosine nucleotide at position 22106220; an insertion at position 22110491; a cytosine nucleotide at position 22113766; an adenine nucleotide at position 22114123; a thymine nucleotide at position 22114140; a cytosine nucleotide at position 22115347; and/or a cytosine at position 22115503, wherein the presence of one, two, three, four or more, all or any combination of the SNPs, insertions and/or deletions indicates that the human subject has an increased risk for coronary heart disease. In one embodiment, the SNP is a cytosine at position 22115503 (rs1333049). In a specific embodiment, the human subject is has an increased risk of myocardial infarction. In a specific embodiment, the human subject has a 10% to 30%, 10% to 25% or 10% to 20% or a 10%, 15%, 25% or 30% a greater likelihood of developing coronary heart disease if one, two, three, four or more, all or any combination of the SNPs, insertions and/or deletions are detected than a human subject in which such SNPs, insertions and/or deletions are not detected. The presence of SNPs in a human subject can be detected using an in vitro assay, e.g., a nucleic acid sample (see Section 5.3 below) and techniques known to one of skill in the art or described in Section 5.4 below.

In another embodiment, the invention provides a method for determining whether a human subject has an increased risk for coronary heart disease (e.g., coronary atherosclerosis or myocardial infarction), comprising detecting whether a guanine nucleotide at position 22086055 (rs10757274) and/or a guanine nucleotide at position 22105026 (rs2383206) of human chromosome 9 is/are present in a human subject, and at least one, two, three, or more, all or any combination of the following SNPs on human chromosome 9: a cytosine nucleotide at position 22062301 (rs9632884), a thymine nucleotide at position 22071850 (rs6475606), a thymine nucleotide at position 22078260 (rs10757272), a guanine at position 22088574 (rs4977574), a guanine nucleotide at position 22088619 (rs2891168), a guanine nucleotide at position 22093813 (rs1333042), a cytosine nucleotide at position 22115347 (rs1333048), and/or a cytosine nucleotide at position 22115503 (rs1333049), wherein the presence of one, two, three, four or more or all of the SNPs indicates that the human subject has an increased risk for coronary heart disease. In a specific embodiment, the human subject is has an increased risk of myocardial infarction. The presence of SNPs in a human subject can be detected using an in vitro assay, e.g., a nucleic acid sample (see Section 5.3 below) and techniques known to one of skill in the art or described in Section 5.4 below.

In another embodiment, the invention provides a method for determining whether a human subject has an increased risk for coronary heart disease (e.g., coronary atherosclerosis or myocardial infarction), comprising detecting whether a guanine at position 22086055 (rs10757274) and a guanine at position 22105026 (rs2383206) of human chromosome 9 are present in human subject, wherein the presence of a guanine at those positions indicates that the human subject has an increased risk for coronary heart disease. In a specific embodiment, the human subject is has an increased risk of myocardial infarction. In some embodiments, the human subject is homozygous at positions 22086055 and 22105026. In a specific embodiment, a human subject that is homozygous at positions 22086055 and 22105026 (i.e., has two guanine nucleotides at those positions) has a greater likelihood for developing coronary heart disease than a human subject heterozygous at those positions. In other embodiments, the human subject is heterozygous at positions 22086055 and 22105026.

In another aspect, the invention provides a method for determining whether a human subject has a polymorphism associated with an increased risk for coronary heart disease (e.g., coronary atherosclerosis or myocardial infarction), comprising detecting whether one or more SNPs in an approximately 58 kb region extending from about 22,062,301 to about 22,120,389 of human chromosome 9 with a p value of less than 0.025 or less than 0.050 (e.g., 0.025, 0.050 or 0.075) is/are present, wherein the presence of the one or more SNPs indicates that the human subject has a polymorphism associated with an increased risk for coronary heart disease. In some embodiments, the human subject is identified as having or determined to have an increased risk for coronary heart disease if the one or more SNPs are detected. In some embodiments, the SNP is in a region extending from position 22,062,301+/−5808, 5000, 4407, 4000, 3000, 2500, 2000, 1500, 1101, 1000, 550, 500, 250, 200, 150, 100, or 50 nucleotides to position 22,120,389+/−5808, 5000, 4407, 4000, 3000, 2500, 2000, 1500, 1101, 1000, 550, 500, 250, 200, 150, 100 or 50 nucleotides of human chromosome 9. In a specific embodiment, the SNP is in a region extending from position 22,062,301 to position 22,120,389 of human chromosome 9. In certain embodiments, in addition to detecting one or more SNPs in a region extending from 22,062,301 to 22,120,389 of human chromosome 9 with a p value of less than 0.025 or less than 0.050, one or more polymorphisms identified as being associated with an increased likelihood of coronary heart disease, such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26:2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2005/0112611, 2007/0031847, 2007/0072821, 2006/0228715, 2006/0223093, and 2005/0272054, each of which are incorporated herein by reference, is also detected. In a specific embodiment, the human subject has an increased risk of myocardial infarction. The presence of the SNPs can be detected using an in vitro assay, e.g., a nucleic acid sample (Section 5.3 below) and techniques known to one of skill in the art or described in Section 5.4 below. In certain embodiments, the presence of one or more or any combination of the SNPs listed in Table 7, Table 8, Table 10 and/or Table 11 are detected. In certain embodiments, the term "significantly associated" refers to a statistically significant association between coronary heart disease and an allele, a haplotype or a SNP.

In certain embodiments, a person identified as having an increased risk for coronary heart disease is administered a therapy to delay the onset, prevent the onset or slow the progression of coronary heart disease. In some embodiments, a person-identified as having an increased risk for a myocardial infarction is administered a therapy to delay or prevent the onset of a myocardial infarction. In particular embodiments, a person characterized for increased risk for coronary atherosclerosis is treated with a therapy to delay the onset, prevent the onset or slow progression of the coronary atherosclerosis, particularly wherein the therapy comprises a lipid-lowering medication. Non-limiting examples of therapies that may be administered to delay the onset, prevent the onset or slow the progression of coronary heart disease (including myocardial infarction and coronary atherosclerosis), include: aspirin, *digitalis*, ACE (angiotensin converting enzyme) inhibitors, beta blockers, nitrates (such as nitroglycerine), calcium-channel blockers, diuretics, blood cholesterol-lowering agents, and thrombolytic agents. In certain embodiments, a person identified as having an increased risk for coronary heart disease is administered a currently available therapy to prevent or treat heart disease or a therapy that will be developed or identified as having utility to prevent or treat coronary heart disease. In some embodiments, the SNPs, alleles, haplotypes, and other polymorphisms described herein are used to assess a person's responsiveness to a therapy for coronary heart disease.

In some embodiments, a person identified as having an increased risk for coronary heart disease adopts one or more lifestyle changes alone or in combination with receiving one or more therapies to delay the onset, prevent the onset, or slow the progression of coronary heart disease (including myocardial infarction and coronary atherosclerosis). Non-limiting examples of lifestyle changes include: stopping smoking cigarettes, lowering high blood pressure, reducing high blood cholesterol, losing extra weight, becoming physically active, and managing diabetes.

5.2. Characteristics of Human Subjects

In certain embodiments, the human subject evaluated for an increased risk for coronary heart disease in accordance with the methods of the invention is a human adult. In some embodiments, the human subject evaluated for an increased risk for coronary heart disease in accordance with the methods of the invention is an elderly human. In some embodiments, the human subject evaluated for an increased risk for coronary heart disease in accordance with the methods of the invention is a human infant. In some embodiments, the human subject evaluated for an increased risk for coronary heart disease in accordance with the methods of the invention is a human child or human toddler. In particular embodiments, the human subject evaluated for an increased risk for coronary heart disease in accordance with the methods of the invention is a 40 to 85 year old human, a 50 to 85 year old human, a 50 to 75 year old human, a 50 to 70 year old human, a 50 to 65 year old human, a 55 to 85 year old human, a 55 to 80 year old human, a 55 to 75 year old human, a 55 to 65 year old human, a 71.1 to 79.7 year old human, a 45 to 64 year old human, a 48 to 60 year old human or a 42 to 72 year old human. In specific embodiments, the human subject evaluated for an increased risk for coronary heart disease in accordance with the methods of the invention is a 45 year old human, a 50 year old human, a 53 year old, a 54 year old human, a 55 year old human, a 56 year old human, a 57 year old human, a 58 year old human, a 59 year old human, a 60 year old human, a 65 year old human, a 70 year old human, a 72 year old human, a 75 year old human, an 80 year old human or an 85 year old human.

In certain embodiments, the human subject evaluated for an increased risk for coronary heart disease in accordance with the methods of the invention is a female. In other embodiments, the human subject evaluated for an increased risk for coronary heart disease in accordance with the methods of the invention is a male.

In certain embodiments, the human subject evaluated for an increased risk for coronary heart disease in accordance with the methods of the invention is a black, a white, an Indian or an Asian. In some embodiments, the human subject evaluated for an increased risk for coronary heart disease in accordance with the methods of the invention is Caucasian. In certain embodiments, the human subject evaluated for an increased risk for coronary heart disease in accordance with the methods of the invention is an African American. In other embodiments, the human subject evaluated for an increased risk for coronary heart disease in accordance with the methods of the invention is not African American. In some embodiments, the human subject evaluated for an increased risk for coronary heart disease in accordance with the methods of the invention is Asian.

In certain embodiments, the human subject evaluated for an increased risk for coronary heart disease in accordance with the methods of the invention smokes cigarettes. In some embodiments, the human subject evaluated for an increased risk for coronary heart disease in accordance with the methods of the invention has a triglyceride level of between 150 to 199 mg/dL, 200 to 499 mg/dL, or 500 mg/dL or more. In particular embodiments, the human subject evaluated for an increased risk for coronary heart disease in accordance with the methods of the invention has a triglyceride level of at least 175 mg/dL, at least 180 mg/dL, at least 185 mg/dL, at least 190 mg/dL, at least 195 mg/dL, at least 200 mg/dL, at least 225 mg/dL, or at least 250 md/dL. In certain embodiments, the human subject evaluated for an increased risk for coronary heart disease in accordance with the methods of the invention has a triglyceride level of less than 150 mg/dL.

In certain embodiments, the human subject evaluated for an increased risk for coronary heart disease in accordance with the methods of the invention has a total cholesterol level of between 200 to 239 mg/dL. In other embodiments, the human subject evaluated for an increased risk for coronary heart disease in accordance with the methods of the invention has a total cholesterol level of 240 mg/dL or more. In yet other embodiments, the human subject evaluated for an increased risk for coronary heart disease in accordance with the methods of the invention has a total cholesterol level of less than 200 mg/dL or less than 280 mg/dL.

In some embodiments, the human subject evaluated for an increased risk for coronary heart disease in accordance with the methods of the invention has been diagnosed as having diabetes. In other embodiments, the human subject evaluated for an increased risk for coronary heart disease in accordance with the methods of the invention does not have or has yet to be diagnosed as having diabetes. In specific embodiments, the human subject evaluated for an increased risk for coronary heart disease in accordance with the methods of the invention has a total cholesterol level of less than 280 mg/dL and does not have or has not been diagnosed with diabetes.

In certain embodiments, the human subject evaluated for an increased risk for coronary heart disease in accordance with the methods of the invention has hypertension. In certain embodiments, the human subject evaluated for an increased risk for coronary heart disease in accordance with the methods of the invention has a normal body mass index (BMI) of 18.5-24.9. In other embodiments, the human subject evaluated for an increased risk for coronary heart disease in accordance with the methods of the invention has an overweight BMI of 25-29.9. In yet other embodiments, the human subject evaluated for an increased risk for coronary heart disease in accordance with the methods of the invention has an obese BMI of 30 or more.

In some embodiments, the human subject evaluated for an increased risk for coronary heart disease in accordance with the methods of the invention has a family history of coronary heart disease. In one embodiment, the human subject evaluated for an increased risk for coronary heart disease in accordance with the methods of the invention has a family history of coronary atherosclerosis. In another embodiment, the human subject evaluated for an increased risk for coronary heart disease in accordance with the methods of the invention has a family history of myocardial infarction. In another embodiment, the human subject evaluated for an increased risk for coronary heart disease in accordance with the methods of the invention has a family history of angina.

In certain embodiments, the human subject evaluated for an increased risk for coronary heart disease in accordance with the methods of the invention do not have a history of cardiovascular symptoms. Non-limiting examples of cardiovascular symptoms include a positive stress test, coronary angiography demonstrating stenosis (>50%) in any artery, and clinical cardiovascular events.

In certain embodiments, the human subject evaluated for an increased risk for coronary heart disease in accordance with the methods of the invention has one, two, three or more characteristics of the population of human subjects used in the studies discussed in the working example. In a specific embodiment, the human subject evaluated for an increased risk for coronary heart disease in accordance with the methods of the invention has one, two, three or more characteristics of the population of human subjects used in the Ottawa Heart Study discussed in the working example. In another embodiment, the human subject evaluated for an increased risk for coronary heart disease in accordance with the methods of the invention has one, two, three or more characteristics of the population of human subjects used in the Atherosclerosis Risk in Communities Study discussed in the working example. In another embodiment, the human subject evaluated for an increased risk for coronary heart disease in accordance with the methods of the invention has one, two, three or more characteristics of the population of human subjects used in the Copenhagen City Heart Study discussed in the working example. In another embodiment, the human subject evaluated for an increased risk for coronary heart disease in accordance with the methods of the invention has one, two, three or more characteristics of the population of human subjects used in the Dallas Heart Study.

5.3. Biological Sample from Human Subjects for Screening

Samples for use in accordance with the methods of the invention include human biological samples comprising genomic DNA and/or RNA, and samples isolated, obtained and/or derived from a human biological sample which samples comprise human genomic DNA, amplified genomic DNA, RNA, amplified RNA and/or cDNA (i.e., a nucleic acid sample). In certain embodiments, in addition to the biological sample itself or in addition to material derived from the biological sample, such as cells and genomic DNA, the sample used in the methods of this invention comprises, for example, added water, salts, glycerin, glucose, an antimicrobial agent, paraffin, a chemical stabilizing agent, heparin, an anticoagulant, and/or a buffering agent.

A sample derived from a biological sample is one in which the biological sample has been subjected to one or more pretreatment steps prior to use in accordance with the methods of the invention. In certain embodiments, a biological fluid is pretreated by centrifugation, filtration, precipitation, dialysis, or chromatography, or by a combination of such pretreatment steps. In other embodiments, a tissue sample is pretreated by freezing, chemical fixation, paraffin embedding, dehydration, permeablization, or homogenization followed by centrifugation, filtration, precipitation, dialysis, or chromatography, or by a combination of such pretreatment steps. In certain embodiments, the sample is pretreated by adjusting the concentration of nucleic acid in the sample, by adjusting the pH or ionic strength of the sample, or by removing contaminating proteins, nucleic acids, lipids, or debris from the sample.

A biological sample containing genomic DNA and/or RNA can be obtained from any tissue or organ in a human subject. Representative biological samples from a human subject include, without limitation, nasal swabs, throat swabs, dermal swabs, blood (including blood culture), buccal swabs, lymph, lung tissue, ejaculatory fluid, saliva, sputum, vaginal secretions, stool, tears, spinal fluid, and synovial fluid. A biological sample can be stored (e.g., at approximately 220 C, 4° C., −20° C. or below −60° C.) before use.

In a specific embodiment, the biological sample is a blood sample. A blood sample may be obtained from a subject according to methods well known in the art. Blood may be drawn from a subject from any part of the body (e.g., a finger, a hand, a wrist, an arm, a leg, a foot, an ankle, a stomach, or a neck) using techniques known to one of skill in the art, in particular methods of phlebotomy known in the art. In a specific embodiment, venous blood is obtained from a subject and utilized in accordance with the methods of the invention. In another embodiment, arterial blood is obtained and utilized in accordance with the methods of the invention. For routine blood tests, venous blood is generally used.

In some embodiments of the present invention, blood is collected and/or stored in a K₃/EDTA tube. In a specific embodiment, blood is collected and/or stored in ACD-A tubes (Becton Dickinson Catalog No. 364606). In another embodiment, blood is collected and/or stored on one, two, three, four or more FAST TECHNOLOGY FOR ANALYSIS (FTA®) cards, such as FTA® Classic Cards, FTA® MINI CARDS, FTA® MICRO CARDS, and FTA® GENE CARDS (Whatman).

In some embodiments, the collected blood is stored prior to use. In one embodiment, the collected blood is stored at room temperature (i.e., approximately 22° C.). In another embodiment, the collected blood is stored at refrigerated temperatures, such as 4° C., prior to use. In some embodiments, a portion of the blood sample is used in accordance with the invention at a first instance of time whereas one or more remaining portions of the blood sample is stored for a period of time for later use. This period of time can be an hour or more, a day or more, a week or more, a month or more, a year or more, or indefinitely. For long term storage, storage methods well known in the art, such as storage at cryo temperatures (e.g. below −60° C.) can be used. In some embodiments, in addition to storage of the blood or instead of storage of the blood, isolated nucleic acids (e.g., isolated genomic DNA) is stored for a period of time for later use. Storage of such nucleic acids can be for an hour or more, a day or more, a week or more, a month or more, a year or more, or indefinitely.

In some embodiments of the present invention, blood cells are separated from whole blood collected from a subject using techniques known in the art. For example, blood collected from a subject can be subjected to Ficoll-Hypaque (Pharmacia) gradient centrifugation. Such centrifugation separates erythrocytes (red blood cells) from various types of nucleated cells and from plasma.

Blood cells can be sorted using a fluorescence activated cell sorter (FACS). Fluorescence activated cell sorting (FACS) is a known method for separating particles, including cells, based on the fluorescent properties of the particles. See, for example, Kamarch, 1987, Methods Enzymol 151: 150-165. Magnetic beads can also be used to separate blood cells in some embodiments of the present invention. Separated blood cells (e.g., leukocytes) can be frozen by standard techniques prior to use in the present methods.

In some embodiments, blood cells are immortalized and/or proliferated in cell culture prior to use or storage. Any technique known in the art for immortalizing and/or proliferating blood cells can be used in accordance with the invention. In certain embodiments, the blood cells (e.g., lymphocytes) are infected with a virus, such as HTLV-I or HTLV-II, that immortalizes the cells. In other embodiments, the blood cells are transformed with an oncogene, such as bcl-2, that immortalizes the cells. In some embodiments, the blood cells are stored prior to or after proliferation and/or immortalization. In one embodiment, the blood cells are stored at cryo temperatures (e.g. below −60° C.).

In another embodiment, the biological sample collected from a human subject is a swab of buccal cells from a subject's inner cheek (i.e., a cheek or buccal swab). In another embodiment, the biological sample is a tissue sample that comprises nucleated cells. In a particular embodiment, the tissue sample is breast, colon, lung, liver, ovarian, pancreatic, heart, prostate, renal, bone or skin tissue. In a specific embodiment, the tissue sample is a biopsy. Techniques for collecting biological samples are known to those of skill in the art.

In some embodiments, the collected cheek swab or tissue sample is stored prior to use. In one embodiment, the collected cheek swab or tissue sample is stored at room temperature (e.g., approximately 22° C.). In another embodiment, the collected cheek swab or tissue sample is stored at refrigerated temperatures, such as 4° C., prior to use. In some embodiments, a portion of the tissue sample is used in accordance with the invention at a first instance of time whereas one or more remaining portions of the tissue sample is stored for a period of time for later use. This period of time can be an hour or more, a day or more, a week or more, a month or more, a year or more, or indefinitely. For long term storage, storage methods well known in the art, such as storage at cryo temperatures (e.g. below −60° C.) can be used. In some embodiments, in addition to storage of the cheek swab or tissue sample, or instead of storage of the cheek swab or tissue sample, isolated nucleic acids (e.g., isolated genomic DNA) is stored for a period of time for later use. Storage of such nucleic acids can be for an hour or more, a day or more, a week or more, a month or more, a year or more, or indefinitely.

A tissue sample can be separated into cell types such as epithelial cells, fibroblasts, etc. and such cell types can be used in accordance with the invention. In some embodiments, cells are immortalized and/or proliferated in cell culture prior to use or storage. Any technique known in the art for immortalizing and/or proliferating cells can be used in accordance with the invention. In certain embodiments, the cells (e.g., lymphocytes) are infected with a virus that immortalizes the cells. In other embodiments, the cells are transformed with an oncogene, such as bcl-2, that immortalizes the cells. In some embodiments, the cells isolated from a cheek swab or tissue sample are stored prior to or after proliferation and/or immortalization. In one embodiment, the cells are stored at cryo temperatures (e.g. below −60° C.).

In some embodiments, after a biological sample is obtained from a human subject, the biological sample is subjected to one or pretreatment steps. In one embodiment, after a biological sample is obtained from a human subject, genomic DNA is extracted. In another embodiment, after a biological sample is obtained from a human subject, cells (e.g., cells of a particular type, such as T-lymphocytes) are cultured and the genomic DNA from the cultured cells is extracted. In some embodiments, extracted genomic DNA is stored (e.g., at approximately 4° C. or below −60° C.) before use. In certain embodiments, extracted genomic DNA is amplified before use in accordance with the methods of the invention. Any technique known to one of skill in the art may be used culture cells, to extract genomic DNA and to amplify genomic DNA.

There are several known methods for extracting genomic DNA from biological samples, any of which can be used in the present invention. One nonlimiting example follows. Between 60-80 mg of tissue is placed in a petri dish with culture media and the tissue is divided into two pieces. The tissue is placed into two sterile 15 ml tubes and centrifuged for two minutes at 4° C. at 1500 rpm. The supernatant is removed and washed twice with 1 ml 1×PBS or DNA-buffer. The supernatant is removed the pellet resuspended in 2.06 ml DNA-buffer. About 100 µl of proteinase K (10 mg/ml) and 240 µl 10% SDS is added, and the solution is shaken gently before incubation overnight at 45° C. in a waterbath. If there are still some tissue pieces visible, proteinase K is added again, the solution shaken gently, and incubated for another 5 hr at 45° C. About 2.4 ml of phenol is then added and the solution is shaken by hand for 5-10 minutes before centrifugation at 3000 rpm for 5 minute at 10° C. The supernatant is pipetted into a new tube, 1.2 ml of phenol is added, 1.2 ml of chloroform/isoamyl alcohol (24:1) is added and then the solution is shaken by hand for 5-10 min before centrifugation at 3000 rpm for 5 minute at 10° C. The supernatant is pipetted into a new tube and 2.4 ml of chloroform/isoamyl alcohol (24:1) is added. The solution is shaken by hand for 5-10 minutes, and centrifuged at 3000 rpm for 5 minutes at 10° C. The supernatant is pipetted into a new tube, 25 µl of 3 M sodium acetate (pH 5.2) is added, 5 ml ethanol is added, and then the solution shaken gently until the DNA precipitates. A glass pipette is heated over a gas burner and the end bent to a hook. The DNA thread is fished out of the solution using the hook and transferred to a new tube. The DNA is washed in 70% ethanol and dried in a speed vacuum. The DNA is dissolved in 0.5-1 ml sterile water overnight (or longer if necessary) at 4° C. on a rotating shaker.

In some embodiments, after a biological sample containing RNA is obtained from a human subject, the biological sample is subjected to one or more pretreatment steps and the RNA is extracted. In certain embodiments, the RNA is amplified or used to produce cDNA. In certain embodiments, the RNA is stored (e.g., at approximately 4° C., 30° C. or −70° C.) before use. Any technique known to one of skill in the art may be used to extract RNA, to amplify and to produce cDNA.

Techniques for isolating nucleic acids include, e.g., those taught in Berger and Kimmel, *Guide to Molecular Cloning Techniques, Methods in Enzymology* volume 152 Academic Press, Inc., San Diego, CA (Berger); Sambrook et al., *Molecular Cloning—A Laboratory Manual* (3rd Ed.), Vol. 1-3, Cold Spring Harbor Laboratory, Cold Spring Harbor, New York, 2001 ("Sambrook"); and/or *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). A plethora of kits are also commercially available for the purification of nucleic acids from cells or other samples (see, e.g., EasyPrep™, FlexiPrep™, both from Pharmacia Biotech; StrataClean™, from Stratagene; and, QIAprep™ from Qiagen).

In some embodiments, a genomic DNA sample, an amplified genomic DNA sample, a RNA sample, an amplified RNA and/or a cDNA is stored (e.g., at approximately 4° C., −30° C. or −70° C.) before use. Techniques for storing such samples are known to one of skill in the art.

In specific embodiments, a sample comprising genomic DNA, amplified DNA, RNA, amplified RNA and/or cDNA isolated, obtained and/or derived from a biological sample from a human subject is added to a buffer to make a suspension and an aliquot of the suspension is used in accordance with the methods of the invention. In some embodiments, a sample of comprising genomic DNA, amplified DNA, RNA, amplified RNA and/or cDNA isolated, obtained and/or derived from a biological sample from a human subject is added to sterile water to make a suspension and an aliquot of the suspension is used in accordance with the methods of the invention.

5.4. Techniques for Detecting Polymorphic Sites

Polymorphisms may be detected using any established method available in the art, including, without limitation, Southern blotting, allele specific hybridization (ASH), detection of single nucleotide extension, sequencing, array hybridization (optionally including ASH), amplified fragment length polymorphism (AFLP) detection, amplified variable sequence detection, randomly amplified polymorphic DNA (RAPD) detection, restriction fragment length polymorphism-(RFLP) detection, self-sustained sequence replication detection, simple sequence repeat (SSR) detection, single-strand conformation polymorphisms (SSCP) detection, northern analysis, quantitative amplification of mRNA or cDNA, or the like. Any of these techniques are readily adapted to high throughput analysis.

In one embodiment, the presence or absence of a polymorphism is determined by genotyping or nucleotide sequencing using techniques known to one of skill in the art. Exemplary genotyping methods are described in Chen et al., "Single nucleotide polymorphism genotyping: biochemistry, protocol, cost and throughput", Pharmacogenomics J. 2003; 3(2):77-96; Kwok et al., "Detection of single nucleotide polymorphisms", Curr Issues Mol Biol. 2003 April; 5(2): 43-60; Shi, "Technologies for individual genotyping: detection of genetic polymorphisms in drug targets and disease genes", Am J Pharmacogenomics. 2002; 2(3):197-205; and Kwok, "Methods for genotyping single nucleotide polymorphisms", Annu Rev Genomics Hum Genet 2001; 2:235-58. Exemplary techniques for high-throughput SNP genotyping are described in Marnellos, "High-throughput SNP analysis for genetic association studies", Curr Opin Drug Discov Devel. 2003 May; 6(3):317-21. Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. For example, mass spectrometry may be used for genotyping. Mass spectrometry takes advantage of the unique mass of each of the four nucleotides of DNA. Polymorphisms can be unambiguously genotyped by mass spectrometry by measuring the differences in the mass of nucleic acids having alternative alleles. MALDI-TOF (Matrix Assisted Laser Desorption Ionization—Time of Flight) mass spectrometry technology is preferred for extremely precise determinations of molecular mass. The following references provide information describing mass spectrometry-based methods for SNP genotyping: Bocker, "SNP and mutation discovery using base-specific cleavage and MALDI-TOF mass spectrometry", Bioinformatics. 2003 July; 19 Suppl 1:144-153; Storm et al., "MALDI-TOF mass spectrometry-based SNP genotyping", Methods Mol Biol. 2003; 212:241-62; Jurinke et al., "The use of MassARRAY technology for high throughput genotyping", Adv Biochem Eng Biotechnol. 2002; 77:57-74; and Jurinke et al., "Automated genotyping using the DNA MassArray technology", Methods Mol Biol. 2002; 187:179-92.

Procedures for performing Southern blotting, standard amplification (PCR, LCR, or the like) and many other nucleic acid detection methods are well established and are taught, e.g., in Sambrook et al., *Molecular Cloning—A Laboratory Manual* (3rd Ed.), Vol. 1-3, Cold Spring Harbor Laboratory, Cold Spring Harbor, New York, 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel"))

and *PCR Protocols A Guide to Methods and Applications* (Innis et al. eds) Academic Press Inc. San Diego, CA (1990) (Innis).

In some embodiments, a polymorphism is detected using unamplified genomic DNA by, e.g., performing a Southern blot on a sample of genomic DNA. In other embodiments, a polymorphism is detected using amplified genomic DNA or cDNA.

Some techniques for detecting polymorphisms utilize hybridization of a nucleic acid probe to nucleic acids corresponding to the polymorphism (e.g., amplified nucleic acids produced using genomic DNA as a template). Hybridization formats, including, but not limited to: solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York, as well as in Sambrook, Berger and Ausubel.

Briefly, restriction fragment length polymorphisms (RFLP) generally involves hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Identifying one or more restriction enzymes that produces informative fragments for each allele of a marker is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Some techniques for detecting polymorphisms comprise an amplification step. Examples of such techniques include, but are not limited to, the polymerase chain reaction (PCR), reverse transcription PCR (RT-PCR), the ligase chain reaction (LCR), Qβ-replicase amplification and other RNA polymerase mediated techniques (e.g., NASBA). For references describing such techniques see, e.g., Innis, Sambrook, Ausubel, and Berger. Additional details are found in Mullis et al. (1987) U.S. Pat. No. 4,683,202; Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of amplifying large nucleic acids by PCR, which is useful in the context of positional cloning, are further summarized in Cheng et al. (1994) *Nature* 369: 684, and the references therein, in which PCR amplicons of up to 40 kb are generated. Methods for long-range PCR are disclosed, for example, in U.S. Pat. No. 6,898,531, issued May 24, 2005, entitled "Algorithms for Selection of Primer Pairs"; U.S. patent application Ser. No. 10/236,480, filed Sep. 9, 2002, entitled "Methods for Amplification of Nucleic Acids"; and U.S. Pat. No. 6,740,510, issued May 25, 2004, entitled "Methods for Amplification of Nucleic Acids". U.S. Ser. No. 10/341,832 (filed Jan. 14, 2003) also provides details regarding primer picking methods for performing short range PCR.

Real time PCR or LCR may be performed on amplification mixtures, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intramolecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone et al. (1995) "Molecular beacon probes combined with amplification by NASBA enable homogenous real-time detection of RNA." *Nucleic Acids Res.* 26:2150-2155; Tyagi and Kramer (1996) "Molecular beacons: probes that fluoresce upon hybridization" *Nature Biotechnology* 14:303-308; Blok and Kramer (1997) "Amplifiable hybridization probes containing a molecular switch" *Mol Cell Probes* 11:187-194; Hsuih et al. (1997) "Novel, ligation-dependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Bonnet et al. (1999) "Thermodynamic basis of the chemical specificity of structured DNA probes" *Proc. Natl. Acad. Sci. U.S.A.* 96:6171-6176; Fang et at (1999) "Designing a novel molecular beacon for surface-immobilized DNA hybridization studies" *J. Am. Chem. Soc.* 121:2921-2922; Marras et al. (1999) "Multiplex detection of single-nucleotide variation using molecular beacons" *Genet. Anal. Biomol. Eng.* 14:151-156; and Vet et al. (1999) "Multiplex detection of four pathogenic retroviruses using molecular beacons" *Proc. Natl. Acad. Sci. U.S.A.* 96:6394-6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

PCR detection and quantification using dual-labeled fluorogenic oligonucleotide probes, commonly referred to as "TaqMan™" probes, can also be performed. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, CA) as well as from a variety of specialty vendors such as Biosearch Technologies (e.g., black hole quencher probes). Further details regarding dual-label probe strategies can be found, e.g., in International Publication No. WO 92/02638.

Other similar methods include e.g. fluorescence resonance energy transfer between two adjacently hybridized probes, e.g., using the "LightCycler®" format described in U.S. Pat. No. 6,174,670.

Self-sustained sequence replication can be used to identify polymorphisms. Self-sustained sequence replication refers to a method of nucleic acid amplification using target nucleic acid sequences which are replicated exponentially, in vitro, under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymophisms (AFLP) can also be used to identify polymorphisms (Vos et al. (1995) *Nucl Acids Res* 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping (Becker et al. (1995) *Mol Gen Genet* 249:65; and Meksem et al. (1995) *Mol Gen Genet* 249:74).

Allele-specific hybridization (ASH) can be used to identify polymorphisms. ASH technology is based on the stable annealing of a short, single-stranded, oligonucleotide probe to a completely complementary single-strand target nucleic acid. Detection may be accomplished via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms may be detected by differential migration patterns of an amplicon comprising the SNP on e.g., an acrylamide gel. However, alternative modes of detection, such as hybridization, e.g., ASH, or RFLP analysis are also appropriate.

5.4.1 Primers and Probes

Primers can readily be designed and synthesized by one of skill in the art for the nucleic acid region of interest. It will be appreciated that suitable primers to be used with the invention can be designed using any suitable method. Primer selection for long-range PCR is described, e.g., in U.S. Pat. No. 6,898,531, issued May 24, 2005, entitled "Algorithms for Selection of Primer Pairs" and U.S. Ser. No. 10/236,480, filed Sep. 5, 2002; for short-range PCR, U.S. Ser. No. 10/341,832, filed Jan. 14, 2003 provides guidance with respect to primer selection. Also, there are publicly available programs such as "Oligo" and LASERGENE® available for primer design. With such available primer selection and design software, the publicly available human genome sequence and the polymorphism locations provided, one of skill can design primers to amplify the SNPs of the present invention.

In some embodiments, the primers are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose or acrylamide gel electrophoresis. In some embodiments, ethidium bromide staining of the PCR amplicons following size resolution allows visualization of the different size amplicons.

The primers are not limited to generating an amplicon of any particular size. For example, the primers used to amplify the polymorphisms are not limited to amplifying the entire region of the RA-CHR9 allele. The primers can generate an amplicon of any suitable length. In some embodiments, the amplification produces an amplicon at least 20 nucleotides in length, or alternatively, at least 50 nucleotides in length, or alternatively, at least 100 nucleotides in length, or alternatively, at least 200 nucleotides in length.

Nucleic acid probes for detecting polymorphisms can be cloned and/or synthesized. It will be appreciated that the precise probe to be used for detection of a nucleic acid comprising a SNP can vary. Any suitable label can be used with a nucleic acid probe. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (2003) *Handbook of Fluorescent Probes and Research Chemicals Ninth Edition* by Molecular Probes, Inc. (Eugene OR).

A primer or probe is typically at least about 8 nucleotides in length. In one embodiment, a primer or a probe is at least about 10 nucleotides in length. In a specific embodiment, a primer or a probe is at least about 12 nucleotides in length. In another specific embodiment, a primer or probe is at least about 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific embodiment, a primer or a probe is within the length of about 18 and about 28 nucleotides. However, in other embodiments, such as nucleic acid arrays and other embodiments in which probes are affixed to a substrate, the probes can be longer, such as on the order of 30-70, 75, 80, 90, 100, or more nucleotides in length.

For analyzing SNPs, it can be appropriate to use oligonucleotides specific for alternative SNP alleles. Such oligonucleotides which detect single nucleotide variations in target sequences may be referred to by such terms as "allele-specific oligonucleotides," "allele-specific probes," or "allele-specific primers." The design and use of allele-specific probes for analyzing polymorphisms is described in, e.g., Mutation Detection A Practical Approach, ed. Cotton et al. Oxford University Press, 1998; Saiki et al., Nature 324, 163-166 (1986); Dattagupta, EP235,726; and Saiki, WO 89/11548.

While the design of each allele-specific primer or probe depends on variables such as the precise composition of the nucleotide sequences flanking a SNP position in a target nucleic acid molecule, and the length of the primer or probe, another factor in the use of primers and probes is the stringency of the condition under which the hybridization between the probe or primer and the target sequence is performed. Higher stringency conditions utilize buffers with lower ionic strength and/or a higher reaction temperature, and tend to require a more perfect match between probe/primer and a target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence. By way of example and not limitation, exemplary conditions for high stringency hybridization conditions using an allele-specific probe are as follows: Prehybridization with a solution containing 5x. standard saline phosphate EDTA (SSPE), 0.5% $NaDodSO_4$ (SDS) at 55° C., and incubating probe with target nucleic acid molecules in the same solution at the same temperature, followed by washing with a solution containing 2xSSPE, and 0.1% SDS at 55° C. or room temperature. Moderate stringency hybridization conditions may be used for allele-specific primer extension reactions with a solution containing, e.g., about 50 mM KCl at about 46° C. Alternatively, the reaction may be carried out at an elevated temperature such as 60° C. In another embodiment, a moderately stringent hybridization condition suitable for oligonucleotide ligation assay (OLA) reactions wherein two probes are ligated if they are completely complementary to the target sequence may utilize a solution of about 100 mM KCl at a temperature of 46° C.

In a hybridization-based assay, allele-specific probes can be designed that hybridize to a segment of target DNA from one individual but do not hybridize to the corresponding segment from another individual due to the presence of different polymorphic forms (e.g., alternative SNP alleles/nucleotides) in the respective DNA segments from the two individuals. Hybridization conditions should be sufficiently stringent that there is a significant detectable difference in hybridization intensity between alleles, and preferably an essentially binary response, whereby a probe hybridizes to only one of the alleles or significantly more strongly to one allele. While a probe may be designed to hybridize to a target sequence that contains a SNP site such that the SNP site aligns anywhere along the sequence of the probe, the probe is preferably designed to hybridize to a segment of the target sequence such that the SNP site aligns with a central position of the probe (e.g., a position within the probe that is at least three nucleotides from either end of the probe). This design of probe generally achieves good discrimination in hybridization between different allelic forms.

Allele-specific probes are often used in pairs (or, less commonly, in sets of 3 or 4, such as if a SNP position is known to have 3 or 4 alleles, respectively, or to assay both strands of a nucleic acid molecule for a target SNP allele), and such pairs may be identical except for a one nucleotide mismatch that represents the allelic variants at the SNP position. Commonly, one member of a pair perfectly matches a reference form of a target sequence that has a more common SNP allele (i.e., the allele that is more frequent in the target population) and the other member of the pair perfectly matches a form of the target sequence that has a less common SNP allele (i.e., the allele that is rarer in the target population). In the case of an array, multiple pairs of probes can be immobilized on the same support for simultaneous analysis of multiple different polymorphisms.

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), *Tetrahedron Letts.*, 22(20):1859-1862, e.g., using a commercially available automated synthesizer, e.g., as described in Needham-VanDevanter et al. (1984) *Nucleic Acids Res.*, 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, CA) and many others. Similarly, PNAs can be custom ordered from any of a variety of sources, such as PeptidoGenic (pkim@ccnet.com), HTI Bio-products, inc. (htibio.com), BMA Biomedicals Ltd (U.K.), Bio.Synthesis, Inc., and many others.

5.4.1. Arrays

Array-based detection can be performed to detect polymorphisms. Commercially available arrays, e.g., from Affymetrix (Santa Clara, CA) or other manufacturers be used to detect polymorphisms. Reviews regarding the operation of nucleic acid arrays include Sapolsky et al. (1999) "High-throughput polymorphism screening and genotyping with high-density oligonucleotide arrays." *Genetic Analysis: Biomolecular Engineering* 14:187-192; Lockhart (1998) "Mutant yeast on drugs" *Nature Medicine* 4:1235-1236; Fodor (1997) "Genes, Chips and the Human Genome." *FASEB Journal* 11:A879; Fodor (1997) "Massively Parallel Genomics." *Science* 277: 393-395; and Chee et al. (1996) "Accessing Genetic Information with High-Density DNA Arrays." *Science* 274:610-614. In a specific embodiment, array based detection is the method used for the identification polymorphisms, due to the inherently high-throughput nature of array based detection.

A variety of probe arrays have been described in the literature and can be used in the context of the present invention for detection of polymorphisms that can be correlated to the phenotypes noted herein. For example, DNA probe array chips or larger DNA probe array wafers (from which individual chips would otherwise be obtained by breaking up the wafer) are used in one embodiment of the invention. DNA probe array wafers generally comprise glass wafers on which high density arrays of DNA probes (short segments of DNA) have been placed. Each of these wafers can hold, for example, approximately 60 million DNA probes that are used to recognize longer sample DNA sequences (e.g., from individuals or populations, e.g., that comprise polymorphisms of interest). The recognition of sample DNA by the set of DNA probes on the glass wafer takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a polymorphism found in the nucleic acid is present. One can also use this approach to perform ASH, by controlling the hybridization conditions to permit single nucleotide discrimination, e.g., for SNP identification and for genotyping a sample for one or more SNPs.

The use of DNA probe arrays to obtain allele information typically involves the following general steps: design and manufacture of DNA probe arrays, preparation of the sample, hybridization of sample DNA to the array, detection of hybridization events and data analysis to determine sequence. Preferred wafers are manufactured using a process adapted from semiconductor manufacturing to achieve cost effectiveness and high quality, and are available, e.g., from Affymetrix, Inc of Santa Clara, California.

For example, probe arrays can be manufactured by light-directed chemical synthesis processes, which combine solid-phase chemical synthesis with photolithographic fabrication techniques as employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays can be synthesized simultaneously on a large glass wafer. This parallel process enhances reproducibility and helps achieve economies of scale.

Once fabricated, DNA probe arrays can be used to obtain data regarding presence and/or expression levels for polymorphisms of interest. The DNA samples may be tagged with biotin and/or a fluorescent reporter group by standard biochemical methods. The labeled samples are incubated with an array, and segments of the samples bind, or hybridize, with complementary sequences on the array. The array can be washed and/or stained to produce a hybridization pattern. The array is then scanned and the patterns of hybridization are detected by emission of light from the fluorescent reporter groups. Additional details regarding these procedures are found in the examples below. Because the identity and position of each probe on the array is known, the nature of the DNA sequences in the sample applied to the array can be determined. When these arrays are used for genotyping experiments, they can be referred to as genotyping arrays.

The nucleic acid sample to be analyzed is isolated, amplified and, typically, labeled with biotin and/or a fluorescent reporter group. The labeled nucleic acid sample is then incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labeled nucleic acid, which is now bound to the probe array. Probes that most clearly match the labeled nucleic acid produce stronger signals than those that have mismatches. Since the sequence and position of each probe on the array are known, by complementarity, the identity of the nucleic acid sample applied to the probe array can be identified.

In one embodiment, two DNA samples may be differentially labeled and hybridized with a single set of the designed genotyping arrays. In this way two sets of data can be obtained from the same physical arrays. Labels that can be used include, but are not limited to, cychrome, fluorescein, or biotin (later stained with phycoerythrin-streptavidin after hybridization). Two-color labeling is described in U.S. Pat. No. 6,342,355, incorporated herein by reference in its entirety. Each array may be scanned such that the signal from both labels is detected simultaneously, or may be scanned twice to detect each signal separately.

Intensity data is collected by the scanner for all the polymorphisms for each of the individuals that are tested for presence of the polymorphism. The measured intensities are a measure indicative of the amount of a particular polymorphism present in the sample for a given individual (expression level and/or number of copies of the allele present in an individual, depending on whether genomic or expressed nucleic acids are analyzed). This can be used to determine whether the individual is homozygous or heterozygous for the polymorphism of interest. The intensity data is processed to provide corresponding polymorphism information for the various intensities.

5.5. Kits

Presented herein are kits for detecting the presence of particular polymorphisms. Kits useful in diagnosis and prognosis include reagents comprising, for example, instructions for use and analysis; means for collecting a tissue or cell sample; nucleic acid probes or primers (e.g., for amplification, reverse transcriptase and detection); labels (e.g., for nucleic acids or proteins); microarrays, gels, membranes or other detection apparati; restriction enzymes (e.g., for RFLP analysis); allele-specific probes; and antisense nucleic acids, any of which may be labeled. In a specific embodiment, the instructions recommend that positive and negative controls are run in parallel with test samples. In some embodiments, the kits comprise one or more control elements, e.g., oligonucleotides, such as primers and probes.

In specific embodiments, the kits comprise, in one or more containers, one or more reagents employed in the various methods for detecting a polymorphism, such as: (1) reagents for purifying nucleic acids; (2) primers for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization and washing buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like.

In some embodiments, the kits are PCR kits. In one embodiment, the PCR kit includes the following: (a) primers used to amplify a polymorphism; and (b) buffers and enzymes including DNA polymerase.

In some embodiments, the kits are microarray kits. For nucleic acid micoarray kits, the kits generally comprise probes attached to a solid support surface. The probes may be labeled with a detectable label. In a specific embodiment, the probes are specific for a polymorphism. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

In some embodiments, the kits are microarray kits which do not analyze the whole genome (i.e., they are not genome arrays). In certain embodiments, the oligonucleotides specific for the haplotypes, SNPs or alleles or other polymorphisms described herein in a microarray are spatially arranged in a manner that facilitates quick analysis of results by detecting certain patterns, wherein detection of one pattern indicates that a human subject is at increased risk for coronary heart disease and another pattern indicates that the human is not at increased risk for coronary heart disease. In certain embodiments, the kits comprise one or more control elements e.g., oligonucleotides.

In some embodiments, a kit comprises, in one or more containers, one or more primers and/or one or more probes for detecting an RA-CHR9 allele. In some embodiments, a kit comprises, in one or more containers, one or more primers and/or one or more probes for detecting a risk allele in an approximately 58 kb region extending from about position 22,062,301 to about position 22,120,389 of human chromosome 9. In certain embodiments, the risk allele is in a region extending from position 22062301+/−5808, 5000, 4000, 3000, 2500, 2000, 1101, 1000, 550, 500, 250, 200, 150, 100 or 50 nucleotides to position 22120389+/−5808, 5000, 4000, 3000, 2500, 2000, 1101, 1000, 550, 500, 250, 200, 150, 100 or 50 nucleotides of human chromosome 9. In a specific embodiment, the kit further comprises instructions for detecting an RA-CHR9 allele and evaluating the results. In certain embodiments, the kit further comprises one or more primers and/or one or more probes for detecting a polymorphism identified as being associated with an increased likelihood of coronary heart disease, such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2007/0031847, 2006/0228715, 2006/0223093, 2005/0272054, 2007/0072821 and 2005/0112611 (each of which are incorporated by herein by reference).

In some embodiments, a kit comprises, in one or more containers, one or more primers and/or one or more probes for detecting a human chromosome 9 haplotype comprising a guanine nucleotide at position 22086055 (rs10757274) and/or a guanine nucleotide at position 22105026 (rs2383206). In other embodiments, a kit comprises, in one or more containers, one or more primers and/or probes for detecting a human chromosome 9 haplotype comprising a guanine nucleotide at position 22086055 (rs10757274) and/or a guanine nucleotide at position 22105026 (rs2383206), and at least one, two, three, or more, all or any combination of the SNPs, insertions and/or deletions recited in Table 7, Table 8, Table 10 or Table 11. In specific embodiments, a kit comprises, in one or more containers, one or more primers and/or probes for detecting a haplotype in a region extending from position 22062301+/−5808, 5000, 4000, 3000, 2500, 2000, 1101, 1000, 550, 500, 250, 200, 150, 100 or 50 nucleotides to position 22120389+/−5808, 5000, 4000, 3000, 2500, 2000, 1101, 1000, 550, 500, 250, 200, 150, 100 or 50 nucleotides of human chromosome 9, wherein the haplotype comprises a guanine nucleotide at position 22086055 (rs10757274) and/or a guanine nucleotide at position 22105026 (rs2383206). In a specific embodiment, the kit further comprises instructions for detecting the haplotype and evaluating the results. In certain embodiments, the kit further comprises one or more primers and/or one or more probes for detecting a polymorphism identified as being associated with an increased likelihood of coronary heart disease, such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al.

(2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2005/0112611, 2007/0031847, 2006/0228715, 2006/0223093, 2007/0072821 and 2005/0272054 (each of which are incorporated herein by reference).

In some embodiments, a kit comprises, in one or more containers, one or more primers and/or one or more probes for detecting a polymorphism with a linkage disequilibrium of between 0.5 to 1, 0.5 to 0.90, or 0.5 to 0.80, or 0.5 to 0.75 with a risk allele in an approximately 58 kb region extending from about position 22,062,301 to about position 22,120,389 of human chromosome 9. In some embodiments, the risk allele is in a region extending from position 22,062,301+/−5808, 5000, 4000, 3000, 2500, 2000, 1101, 1000, 550, 500, 250, 200, 150, 100 or 50 nucleotides to position 22,120,389+/−5808, 5000, 4000, 3000, 2500, 2000, 1101, 1000, 550, 500, 250, 200, 150, 100 or 50 nucleotides of human chromosome 9. In a specific embodiment, the kit further comprises instructions for detecting the polymorphism and evaluating the results. In certain embodiments, the kit further comprises one or more primers and/or one or more probes for detecting a polymorphism identified as being associated with an increased likelihood of coronary heart disease, such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166: 28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2007/0031847, 2006/0228715, 2006/0223093, 2007/0072821, 2005/0272054 and 2005/0112611 (each of which are incorporated by herein by reference).

In some embodiments, a kit comprises, in one or more containers, one or more primers and/or one or more probes for detecting one, two, three, four or more, all or any combination of the following SNPs, insertions, and/or deletions listed in Table 7, Table 8, Table 10 and/or Table 11. In a specific embodiment, a kit comprises, in one or more containers, one or more primers or probes for detecting the SNP at rs1075724 and/or the SNP at rs2383206. In another specific embodiment, at kit comprises, in one or more containers, one or more primers and/or probes for detecting the SNP at rs1333049 and/or the SNP at rs10757278. In a specific embodiment, the kit further comprises instructions for detecting the SNPs, insertions and/or deletions and evaluating the results. In certain embodiments, the kit further comprises one or more primers and/or one or more probes for detecting a polymorphism identified as being associated with an increased likelihood of coronary heart disease, such as those described in International Publication No. WO 2007/006862, WO 2004/03576, WO 2004/035741, and WO 2006/105439; Shiffman et al (2005) Am J Hum Genet 77: 596-605; Shiffman et al (2006) Arteriosclerosis, Thrombosis, and Vascular Biology 26: 1613-1618; Iakoubova et al. (2006) Arteriosclerosis, Thrombosis, and Vascular Biology 26: 2763-2768; Morrison et al. (2007) American Journal of Epidemiology 166:28-35; Luke et al. (2007) Arteriosclerosis, Thrombosis, and Vascular Biology 27: 2030-2036; Shiffman et al. (2008) Arteriosclerosis, Thrombosis, and Vascular Biology 28: 173-179; Iakoubova et al. (2008) J Am Coll Cardiol 51: 449-455; Iakoubova et al. (2008) J Am Coll Cardiol 51: 435-443; Shiffman et al. (2008) J Am Coll Cardiol 51:444-448; Bare et al. (2007) Genetics in Medicine 9: 682-689; Helgadottir et al. (2004) Nat. Genet. 36: 233-239; and U.S. Patent Application Publication Nos. 2007/0280917, 2006/0019269, 2005/0282855, 2005/0164220, 2005/0113408, 2005/0112611, 2007/0031847, 2006/0228715, 2006/0223093, 2007/0072821 and 2005/0272054 (each of which are incorporated by herein by reference).

5.6. Systems

Presented herein are systems comprising a kit or a component(s) of the kits presented herein and a computer program product for use in conjunction with a computer system. In such systems, the computer program product can comprise a computer readable storage medium and a computer program mechanism embedded therein. The computer program mechanism may comprise instructions for evaluating the presence of particular polymorphism, in one or a plurality of samples. In some embodiments, the computer program comprises instructions for evaluating the presence of one, two, three or more polymorphisms. In some embodiments, the computer program will comprise instructions that correlate the presence or absence of a polymorphism with a predicted phenotype. The system instructions can compare detected information as to allele sequence or expression level with a database that includes correlations between the alleles and the relevant phenotypes. This database can be multidimensional, thereby including higher-order relationships between combinations of alleles and the relevant phenotypes. These relationships can be stored in any number of look-up tables, e.g., taking the form of spreadsheets (e.g., Excel™ spreadsheets) or databases such as an Access™, SQL™, Oracle™, Paradox™, or similar database. The system includes provisions for inputting sample-specific information regarding allele detection information, e.g., through an automated or user interface and for comparing that information to the look up tables.

In some embodiments, the system instructions can also include software that accepts diagnostic information associated with any detected allele information, e.g., a diagnosis that a subject with the relevant allele has a particular phenotype. This software can be heuristic in nature, using such inputted associations to improve the accuracy of the look up tables and/or interpretation of the look up tables by the system. A variety of such approaches, including neural networks, Markov modeling, and other statistical analysis are described above.

Optionally, system components for interfacing with a user are provided. For example, the systems can include a user viewable display for viewing an output of computer-implemented system instructions, user input devices (e.g., keyboards or pointing devices such as a mouse) for inputting user commands and activating the system, etc. Typically, the system of interest includes a computer, wherein the various computer-implemented system instructions are embodied in computer software, e.g., stored on computer readable media.

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Sequel™, Oracle™, Paradox™) can be adapted to the present invention by inputting a character string corresponding to an allele herein, or an association between an allele and a phenotype. For example, the systems can include software having the appropriate character string information, e.g., used in conjunction with a user interface (e.g., a GUI in a standard operating system such as a Windows, Macintosh or LINUX system) to manipulate strings of characters. Specialized sequence alignment programs such as BLAST can also be incorporated into the systems of the invention for alignment of nucleic acids or proteins (or corresponding character strings) e.g., for identifying and relating multiple alleles.

Systems can include a computer with an appropriate database and an allele sequence or correlation of the invention. Software for aligning sequences, as well as data sets entered into the software system comprising any of the sequences herein can be a feature of the invention. The computer can be, e.g., a PC (Intel x86 or Pentium chip-compatible DOS™, OS2™ WINDOWS™ WINDOWS NT™, WINDOWS95™, WINDOWS98™, WINDOWS2000, WINDOWSME, WINDOWSXP, WINDOWS VISTA or LINUX based machine, a MACINTOSH™, Power PC, or a UNIX based (e.g., SUN™ work station or LINUX based machine) or other commercially common computer which is known to one of skill. Software for entering and aligning or otherwise manipulating sequences is available, e.g., BLASTP and BLASTN, or can easily be constructed by one of skill using a standard programming language such as Visualbasic, Fortran, Basic, Java, or the like.

In some embodiments, the systems include data acquisition modules for detecting one or more polymorphisms (e.g., one or more array comprising one or more biomolecular probes, detectors, fluid handlers, or the like). The biomolecular probes of such a data acquisition module can include any that are appropriate for detecting the polymorphism, e.g., oligonucleotide probes, proteins, aptamers, antibodies, etc. These can include sample handlers (e.g., fluid handlers), robotics, microfluidic systems, nucleic acid or protein purification modules, arrays (e.g., nucleic acid arrays), detectors, thermocyclers or combinations thereof, e.g., for acquiring samples, diluting or aliquoting samples, purifying marker materials (e.g., nucleic acids or proteins), amplifying marker nucleic acids, detecting amplified marker nucleic acids, and the like.

For example, automated devices that can be incorporated into the systems herein have been used to assess a variety of biological phenomena, including, e.g., expression levels of genes in response to selected stimuli (Service (1998) "Microchips Arrays Put DNA on the Spot" *Science* 282: 396-399), high throughput DNA genotyping (Zhang et al. (1999) "Automated and Integrated System for High-Throughput DNA Genotyping Directly from Blood" *Anal. Chem.* 71:1138-1145) and many others. Similarly, integrated systems for performing mixing experiments, DNA amplification, DNA sequencing and the like are also available. See, e.g., Service (1998) "Coming Soon: the Pocket DNA Sequencer" *Science* 282: 399-401. A variety of automated system components are available, e.g., from Caliper Technologies (Hopkinton, MA), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, CA). Similarly, commercially available microfluidic systems that can be used as system components in the present invention include those from Agilent technologies and the Caliper Technologies. Furthermore, the patent and technical literature includes numerous examples of microfluidic systems, including those that can interface directly with microwell plates for automated fluid handling.

Any of a variety of liquid handling and/or array configurations can be used in the systems herein. One common format for use in the systems herein is a microtiter plate, in which the array or liquid handler includes a microtiter tray. Such trays are commercially available and can be ordered in a variety of well sizes and numbers of wells per tray, as well as with any of a variety of functionalized surfaces for binding of assay or array components. Common trays include the ubiquitous 96 well plate, with 384 and 1536 well plates also in common use. Samples can be processed in such trays, with all of the processing steps being performed in the trays. Samples can also be processed in microfluidic apparatus, or combinations of microtiter and microfluidic apparatus.

In addition to liquid phase arrays, components can be stored in or analyzed on solid phase arrays. These arrays fix materials in a spatially accessible pattern (e.g., a grid of rows and columns) onto a solid substrate such as a membrane (e.g., nylon or nitrocellulose), a polymer or ceramic surface, a glass or modified silica surface, a metal surface, or the like. Components can be accessed, e.g., by hybridization, by local rehydration (e.g., using a pipette or other fluid handling element) and fluidic transfer, or by scraping the array or cutting out sites of interest on the array.

The system can also include detection apparatus that is used to detect allele information, using any of the approached noted herein. For example, a detector configured to detect real-time PCR products (e.g., a light detector, such as a fluorescence detector) or an array reader can be incorporated into the system. For example, the detector can be configured to detect a light emission from a hybridization or amplification reaction comprising an allele of interest, wherein the light emission is indicative of the presence or absence of the allele. Optionally, an operable linkage between the detector and a computer that comprises the system instructions noted above is provided, allowing for automatic input of detected allele-specific information to the computer, which can, e.g., store the database information and/or execute the system instructions to compare the detected allele specific information to the look up table.

Probes that are used to generate information detected by the detector can also be incorporated within the system, along with any other hardware or software for using the probes to detect the amplicon. These can include thermocycler elements (e.g., for performing PCR or LCR amplification of the allele to be detected by the probes), arrays upon which the probes are arrayed and/or hybridized, or the like. The fluid handling elements noted above for processing samples, can be used for moving sample materials (e.g., template nucleic acids and/or proteins to be detected) primers, probes, amplicons, or the like into contact with one another. For example, the system can include a set of probes or primers configured to detect at least one allele associated with a phenotype. The detector module is configured to detect one or more signal outputs from the set of probes or primers, or an amplicon produced from the set of probes or primers, thereby identifying the presence or absence of the allele.

The sample to be analyzed is optionally part of the system, or can be considered separate from it. The sample optionally includes e.g., genomic DNA, amplified genomic DNA, cDNA, amplified cDNA, RNA, amplified RNA, proteins, etc., as noted herein.

Some systems presented herein comprise a kit or one or more components of the kits presented herein, a computer having a central processing unit and a memory coupled to the central processing unit. Some systems presented herein comprise a kit or one or more components of the kits presented herein, a computer readable medium, a computer having a central processing unit and a memory coupled to the central processing unit. The memory stores instructions for evaluating the presence of particular polymorphisms. In specific embodiments, the memory stores instructions for evaluating the presence of one, two, three or more polymorphisms. In some embodiments, the memory comprises instructions for transmitting the results of a method presented herein to a remote computer and the remote computer includes instructions for evaluating the presence of one, two, three or more polymorphisms.

In some embodiments, presented herein is a computer system comprising a computer readable medium comprising the results of an evaluation for the presence of particular polymorphisms, as described herein. In some embodiments, a computer system presented herein comprises:

a central processing unit;
a main non-volatile storage unit, for example, a hard disk drive, for storing software and data, the storage unit controlled by storage controller;
a system memory, such as high speed random-access memory (RAM), for storing system control programs, data and application programs, comprising programs and data loaded from non-volatile storage unit, and may also include a read-only memory (ROM);
a user interface, comprising one or more input devices (e.g., a keyboard) and display or other output device;
a network interface card for connecting to any wired or wireless communication network (e.g., a wide area network such as the Internet);
an internal bus for interconnecting the aforementioned elements of the system; and
a power source to power the aforementioned elements.

Operation of the computer can be controlled primarily by an operating system, which is executed by a central processing unit. The operating system can be stored in the system memory. In addition to the operating system, an implementation system may include: a file system for controlling access to the various files and data structures presented herein; a training data set for use in the construction of one or more decision rules in accordance with the methods presented herein; a data analysis algorithm module for processing training data and constructing decision rules; one or more decision rules; a profile evaluation module for determining whether a polymorphism is present.

The computer may comprise software program modules and data structures. Each of the data structures can comprise any form of a data storage system, including, but not limited to, a flat ASCII or binary file, an Excel spreadsheet, a relational database (e.g., SQL), or an on-line analytical processing (OLAP) database (e.g., MDX and/or variants thereof). In some embodiments, such data structures are each in the form of one or more databases that include a hierarchical structure (e.g., a star schema). In some embodiments, such data structures are each in the form of databases that do not have explicit hierarchy (e.g., dimension tables that are not hierarchically arranged).

In some embodiments, each of the data structures stored or accessible to the computer system are single data structures. In other embodiments, such data structures in fact comprise a plurality of data structures (e.g., databases, files, archives) that may or may not all be hosted by the same computer. For example, in some embodiments, a training data set may comprise a plurality of Excel spreadsheets that are stored either on the computer and/or computers that are addressable by the computer across wide area network. In another example, a training set may comprise a database that is either stored on the computer or is distributed across one or more computers that are addressable by the computer across a wide area network.

It will be appreciated that many of the modules and data structures mentioned above can be located on one or more remote computers. For example, in some embodiments, web service-type implementations are used. In such embodiments, an evaluation module can reside on a client computer that is in communication with the computer via a network. In some embodiments, a profile evaluation module can be an interactive web page.

In some embodiments, a training data set and/or decision rules are on a single computer and in other embodiments, one ore more of such data structures and modules are hosted by one or more remote computers. Any arrangement of the data structures and software modules on one or more computers is within the scope the systems presented herein so long as these data structures and software modules are addressable with respect to each other across a network or by other electronic means.

In some embodiments, a digital signal embodied on a carrier wave comprises data with respect to a method presented herein. In some embodiments, a digital signal embodied on a carrier wave comprises a determination as to whether a particular polymorphism is present in a sample. In some embodiments, a graphical user interface is provided for determining whether a polymorphism is present in a sample. The graphical user interface may comprise a display field for displaying a result encoded in a digital signal embodied on a carrier wave received from a remote computer.

6. EXAMPLE: COMMON ALLELE ON CHROMOSOME 9 ASSOCIATED WITH CORONARY HEART DISEASE

This example describes the identification of an approximately 58 kb region of human chromosome 9 associated with an increased risk of coronary heart disease.

Coronary heart disease (CHD) is the single greatest cause of death worldwide (1, 2). Although CHD is highly heritable, the DNA sequence variations that confer cardiovascular risk remain largely unknown. To identify sequence variants associated with CHD, we undertook a genome-wide association study using 100,000 single nucleotide polymorphisms (SNPs). To minimize false positive associations without unduly sacrificing statistical power, the study design comprised three sequential case-control comparisons performed at a nominal significance threshold of P<0.025 (FIG. 1). For the initial genome-wide scan, cases and controls were Caucasian men and women from Ottawa, Canada who participated in the Ottawa Heart Study (OHS). Cases had severe, premature CHD with a documented onset before the age of 60 years and culminating in coronary artery revascularization (Table 1). To limit confounding by factors that strongly predispose to premature CHD, individuals with diabetes or plasma cholesterol levels consistent with monogenic hypercholesterolemia (>280 mg/dL) were excluded. Controls were healthy Caucasian men (>65 y) and women (>70 y) from Ottawa who had no symptoms or history of CHD (Table 1).

Custom oligonucleotide arrays (3) were used to assay 100,000 SNPs arranged at approximately 30 kb intervals throughout the genome in 322 cases and 312 controls (OHS-1). Of these, 9,636 SNPs deviated strongly from Hardy-Weinberg equilibrium (P<0.001) or did not meet quality-control criteria (3) and 17,500 were sub-polymorphic (minor allele frequency <1%) in the sample. The remaining 72,864 SNPs were entered into the analysis and 2,586 were associated with CHD at a nominal significance threshold of 0.025 (Table 2). These 2,586 SNPs were genotyped in an independent sample of 311 cases and 326 controls, from Ottawa (OHS-2) using the same criteria as OHS-1 (Table 1). Of these, 50 were associated with CHD at a nominal significance threshold of 0.025, with the same direction of effect (Table 2).

To limit attrition of true positive associations due to inadequate statistical power, the third case-control comparison was performed in a much larger prospective study of CHD risk, the Atherosclerosis Risk in Communities (ARIC) study, which enrolled and followed 11,478 Caucasians (4). Only two of the 50 SNPs identified in the Ottawa cohorts were significantly associated with incident CHD in the ARIC population (Table 2). These two SNPs, rs10757274 and rs2383206, were located within 20 kb of each other on chromosome 9 and were in strong linkage disequilibrium (r2-0.89).

To validate the association between rs10757274 and rs2383206 and CHD, both SNPs were assayed in three additional independent cohorts: the Copenhagen City Heart Study (CCHS), a prospective study of ischemic heart disease in 10,578 Danish men and women (5); the Dallas Heart Study (DIS), a population-based probability sample of Dallas County residents (6); and a third sample of 647 cases and 847 controls from the Ottawa Heart Study population (OHS-3). In the CCHS, cases were participants who experienced an ischemic cardiovascular event during the 20 yr follow-up period while controls were those who did not develop CHD over the same time interval. In the DHS, cases and controls were defined using electron-beam computer tomography to measure coronary artery calcium, an index of coronary atherosclerosis (7). In OHS-3, cases had documented CHD before the age of 55 (men) or 65 (women) years, whereas controls were men aged >65 and women aged >70 years who did not have symptoms of CHD (Table 1). In all three validation studies, both SNPs were significantly associated with CHD (Table 3).

The magnitude of CHD risk associated with the risk allele was determined by Cox proportional-hazards modeling in the ARIC and CCHS cohorts. The hazard ratios associated with the risk alleles were comparable in the two populations, and indicated a graded increase in risk from noncarriers to heterozygotes to homozygotes (Table 4). The two SNPs (rs10757274 and rs2383206) define an allele that was associated with a ~15-20% increase in risk in the 50% of individuals who were heterozygous for the allele and a ~30-40% increase in CHD in the 25% of Caucasians who were homozygous for the allele. The population attributable risk associated with the risk allele was 12.5-15% in the ARIC population and 10-13% in the CCHS cohort.

Without being bound by theory, it is possible that the association between the risk allele defined by rs10757274 and rs2383206 increases the development of atherosclerotic plaques, promotes thrombogenesis, or increases the tendency of atherosclerotic plaques to rupture. The finding that the risk allele was associated with coronary artery calcification in the DHS and with severe premature atherosclerosis in OHS-1 indicates that it promotes CHD by increasing the atherosclerotic burden. The risk allele was not associated with any of the major risk factors for atherosclerosis in ARIC or CCHS (Tables 5 and 6), and the association remained significant in models that considered multiple possible confounding covariates (including age, gender, plasma lipid levels, blood pressure, diabetes, and plasma C-reactive protein levels, see Table 3). These analyses indicates that the effect of the chromosome 9 risk allele on CHD was not mediated by any of the established risk factors for cardiovascular disease.

To fine-map the locus associated with CHD, we assayed SNPs spaced at ~5 kb intervals across the region extending 175 kb upstream and downstream of rs10757274 and rs2383206 in 500 cases and 500 controls from OHS-2 and OHS-3. Eight additional SNPs at the locus spanning a 58 kb region (extending from 22,062,301 to 22,120,389) were significantly associated with CHD (FIG. 2). All eight were in strong linkage disequilibrium with each other and with rs10757274 and rs2383206. The region demarcated by these SNPs was flanked on both sides by ~50 kb regions in which none of the 30 SNPs tested were associated with CHD. Two of 65 SNPs in the 350 kb region surrounding the 58 kb risk locus were associated with CHD at the nominal significance threshold, but neither was in strong linkage disequilibrium with rs10757274 and rs2383206. These data indicate that the risk allele comprises a single haplotype that spans ~58 kb.

Inspection of the UCSC Genome Browser and BLAST searches against the NCBI nr nucleotide sequence database revealed no annotated genes or microRNAs within the 58 kb interval. A number of spliced ESTs map within the interval, but none contain open reading frames that extend more than a few amino acids. Resequencing of the 58 kb interval in two homozygotes for the risk allele and one homozygote for the reference allele revealed 66 polymorphisms (SNPs plus small insertions or deletions), of which 35 were specific to the risk allele (Table 7). Only one of these variants, a copy number variation in a run of 9 consecutive CAT repeats (extending from nucleotide 22110787 to 22110814, NCBI build 36.1) mapped to a spliced transcript (B1765545) that appears to be part of a large noncoding RNA of unknown function (8). PCR amplification of cDNAs confirmed expression of the transcript in placenta and transformed lymphocytes. Variation in the expression or function of this transcript may be associated with risk of CHD.

Alternatively, the risk allele may alter a regulatory element that affects the expression of a gene located outside of the 58 kb interval. Cross-species sequence alignments revealed several conserved segments within the 58 kb interval that may contain such regulatory elements. It is also possible that the risk allele extends beyond the 58 kb interval defined in this study, that the functional sequence variants that confer risk of CHD are located outside of the interval. Resequencing the coding regions of the two genes most proximal to the risk locus, CDKN2A and CDKN2B revealed only a single variant (A158S in CDKN2A) that was present in 6 of the 96 individuals examined and is thus unlikely to explain the CHD risk associated with the locus. The localization of the risk locus to a region devoid of known genes implicates a previously unrecognized gene or regulatory element that can substantially affect CHD independently of established risk factors.

Comparison of the Yoruba and CEPH data from the HapMap revealed striking ethnic differences in allele frequencies in the risk interval (Table 8). Of the 10 alleles that were significantly associated with CHD in whites, 3 were virtually absent from the Yoruba population, and 6 others much less common. Both rs10757274 and rs2383206 were present at appreciable frequencies among African-Americans in ARIC and DHS, but neither SNP was associated with CHD in either population (Table 9). The apparent ethnic differences in association between these SNPs and CHD in ARIC may reflect differences in statistical power in ARIC, but cannot explain the ethnic differences observed in DHS, where African-Americans are the largest group, indicating that the functional sequence variants associated with the risk allele in whites are less common in African-Americans. This notion is consistent with our finding that the frequencies of several alleles associated with CHD risk factors differ widely among ethnic groups (9-11).

The results of this study illustrate both the perils and the promise of whole-genome association. The initial scan and the first replicate screen both generated substantially more SNPs that achieved the pre-specified significance threshold than would be predicted by chance alone, as indicated by permutation testing (Table 2). Yet only two of these SNPs (comprising one allele) survived further replication, despite the use of a large sample (i.e., ARIC) with high statistical power. This finding highlights the necessity for adequate replication to protect against artifacts that may occur due to population stratification, multiple testing, or other factors to which whole-genome association studies are particularly susceptible. The consistent replication of the chromosome 9 risk allele in six independent study samples indicates that the approach can be productively applied to conditions as complex as CHD, which is known to be influenced by a variety of environmental and genetic factors (12). Furthermore, analysis of 50 randomly selected regions of 500 kb each indicated that the 72,864 informative SNPs used in the initial scan provided 30-40% of the power that would be obtained by assaying all Phase II Hapmap SNPs.

6.1. Materials and Methods

The Ottawa Heart Study. The Ottawa Heart Study is an ongoing, hospital-based study of coronary heart disease at the Ottawa Heart Institute in Ottawa, Canada. The study was approved by the Institutional Review Board at the University of Ottawa Heart Institute and all participants provided written informed consent. All patients at the Institute who undergo coronary artery bypass grafting, coronary artery angiography, or care for acute myocardial infarction are invited to participate in the study. Three independent samples (OHS-1, OHS-2, and OHS-3) were ascertained serially for this study. Caucasian men and women aged <60 y with advanced disease requiring coronary artery bypass grafting or percutaneous coronary intervention who did not have a history of diabetes mellitus or severe dyslipidemia, suggestive of a monogenic lipid disorder (TC>280 mg/dl/7.0 mmol/L) were included in the initial genome-wide scan (OHS-1). Subsequently, a second sample of individuals was recruited using the same clinical criteria (OHS-2). The mean age of onset of CAD in these individuals was 47.8+7.5(SD) years. Once recruitment for OHS-1 and OHS-2 was completed, individuals with documented CHD before the age of 55 (men) or 65 (women) were recruited for OHS-3. Healthy elderly controls (men>65 y, women>70 y) were recruited via an extensive newspaper and television advertising campaign in the Ottawa community. Controls were carefully interviewed by a physician or nurse to ascertain that they were free of symptoms of possible ischemic arterial disease and had no past history of cardiovascular symptoms, a positive stress test, coronary angiography demonstrating stenosis (>50%) in any artery or clinical cardiovascular events. Individuals with the same ethnic background as the cases (Caucasian) were included in this study. The mean age of the control subjects was 74.9+4.8 years. Controls for OHS-1, OHS-2, and OHS-3 were collected sequentially as described for cases.

The Atherosclerosis Risk in Communities Study (ARIC). The ARIC study comprised men and women aged 45 to 64 years who were randomly selected from four communities (Jackson, MS; Minneapolis MN; Forsyth County, NC; and Washington County, MD). The protocol for the study was approved by the institutional review boards of all centers, and all participants provided written informed consent that included consent for genetic studies. Race or ethnic group was determined by self-identification; participants described themselves as black or white in response to a questionnaire on which the available categories were "black", "white", "Indian", or "Asian". Plasma lipids, glucose, insulin and lipoproteins were assayed in the ARIC central lipid laboratory with commercial reagents, as previously described (13-15). Cases had a documented CHD event (defined as myocardial infarction, coronary artery revascularization, or coronary death) during the 15 yr follow-up period of the study; individuals with prevalent disease at the baseline visit were excluded. Controls were individuals who did not develop incident CHD. The study sample delineated by these criteria provides >90% power to detect common alleles (minor allele frequency >0.1) that differ in frequency by 0.06 or more between cases and controls.

The Copenhagen City Heart Study (CCHS). The Copenhagen City Heart Study population was randomly drawn from the Copenhagen Population Register in January 1976 (16). The study was approved by the Danish ethics committee for the City of Copenhagen and Frederiksberg and informed consent was provided according to the Declaration of Helsinki. The sample was drawn from a population of approximately 90 000 inhabitants 20 years and older living within 10 wards surrounding Rigshospitalet, the National University Hospital of Copenhagen. A second examination was performed 5 years later (1981-1983), and a third examination was performed after 15 years (1991-1994), at which time blood samples were obtained from 9,259 individuals for isolation of DNA. A self-administered questionnaire was used to obtain information regarding familial history, education and socio-economic status, and smoking and drinking habits. Plasma cholesterol and triglyceride levels were determined enzymatically using commercial reagents, and HDL-C was determined after removal of apoB-containing lipoproteins by precipitation with phosphotungstic acid and magnesium. Participants were white and of Danish descent.

The Dallas Heart Study. The Dallas Heart Study is a multi-ethnic, population-based probability sample of Dallas County residents. The study was approved by the Institutional Review Board at the University of Texas Southwestern Medical Center and included three phases: an in-home interview, an in-home phlebotomy visit, and a clinic visit during which a variety of imaging examinations were performed. Caucasian men and women who underwent electron-beam computer tomography to assess coronary artery calcification were eligible for the present study. Each individual underwent two consecutive scans. The distribution of CAC scores is extremely skewed and inter-scan variability is high for scores below 10 Agatston units (17), therefore we excluded individuals with CAC scores between 2 and 10 units and divided the population into controls (CAC scores of ≤2 units, n=575) and cases (those with CAC scores≥10 units, n=166), as previously described (5).

Genotyping: Chip-Based Oligonucleotide Hybridization: SNP Selection.

Using NCBI Build 34, the genome was partitioned into blocks of 13 kb, and one SNP was selected from each block. Using a whole-genome multi-ethnic haplotype map (18), we preferentially chose common haplotype defining SNPs, then common SNPs, then rare SNPs. Where no previously characterized SNPs were available, we chose validated SNPs from dbSNP. Ties were broken so as to minimize variation in inter-SNP spacing. This yielded roughly 200,000 SNPs, of which 70% were haplotype defining, and another 10% were common, 4% were rare, and 16% were from dbSNP. Every other SNP was selected, yielding a set of ~100,000. Using performance data for these assays on another array design to identify failing assays, we selected replacement SNPs from the multi-ethnic map to fill the largest gaps.

Genotyping. Genotyping was performed by Perlegen Sciences using custom high-density oligonucleotide arrays. Each SNP was interrogated by 24 different 25mer oligonucleotide probes synthesized on a glass substrate. The 24 features comprise four sets of six features interrogating both reference and alternate alleles on forward and reference strands. Each allele and strand is represented by oligonucleotides with the variant nucleotides a five offset positions: 22, 21, 0, 1 and 2, (where the number indicates the position of the SNP within the 25mer, with 0 being the 13th base). At offset 0, a quartet was tiled, which includes the perfect match to reference and alternate SNP alleles and the two remaining nucleotides as mismatch probes. When possible, the mismatch features were selected to match a purine nucleotide substitution with a purine nucleotide and a pyrimidine nucleotide with a pyrimidine nucleotide.

The reliability of the intensity measurements of each SNP was assessed using two methods. One metric, "conformance", indicates the presence of specific target DNA for that SNP. The other metric, "signal to background ratio", measures the relative amounts of specific and nonspecific binding. SNPs that failed to meet specified cutoffs on both metrics were discarded. Conformance was computed independently for the two allele feature sets, and a maximum was taken of the two values. Conformance of a given allele is defined as the fraction of feature sets for which the perfect-match feature is brighter than the corresponding mismatch feature. SNP measurements having conformance scores<0.9 were discarded. The signal to background ratio was calculated from intensity measurements for both alleles, as the root mean square of trimmed mean intensities for the perfect-match features for each allele, divided by the corresponding value for the mismatch features. SNP measurements having signal/background<1.5 were discarded.

Calling Algorithm. Individual genotypes for a SNP were determined by clustering measurements from multiple scans in the two-dimensional space defined by background-adjusted trimmed mean intensities of the perfect-match features for each allele. A K-means algorithm was used to assign measurements to clusters representing distinct diploid genotypes. The average call rate was 98.54 percent.

Mass Spectrometry. The 50 sequence variants identified in the genome-wide scan were assayed in the ARIC population by mass spectrometry using the Sequenom MassARRAY system (Sequenom, Inc.; San Diego, CA).

Fluorogenic 5'-nucleotidase assays for rs10757274 and rs2383206 were developed with the use of the TaqMan assay system (Applied Biosystems). The assays were performed on a 7900HT Fast Real-Time PCR instrument with probes and reagents purchased from Applied Biosystems.

DNA sequencing. The 58 kb interval between rs12555547 and rs10965244 was sequenced in two individuals homozygous for the risk allele, and in one individual homozygous for the wild-type allele as described (19). The coding region and flanking intronic sequences of CDKN2A and CDKN2B were sequenced in 96 arbitrarily selected Caucasian men. All sequence variants identified were verified by manual inspection of the chromatograms and missense changes were confirmed by an independent resequencing reaction.

Reverse transcription and PCR Amplification of cDNAs. RNA was isolated from human, placenta, and EBV-transformed lymphocytes by a modified phenol-chloroform extraction (TRIZOL reagent, Invitrogen Corporation, Carlsbad, CA), and reverse transcribed (SuperScript III First-strand synthesis system, Invitrogen). Aliquots of cDNA were amplified using primers directed against spliced ESTs CN277071, BX100299 and DQ485453.

Statistical Analysis. For the genome-wide scan, allelic associations were evaluated for each SNP using chi-square tests on 2×2 contingency tables with no adjustments. Calculations were performed independently at Perlegen Sciences and at UT Southwestern and essentially identical results were obtained. To determine the empirical P-values we randomized the sample case/control status 1,000 times, and calculated allelic associations on each permuted dataset. SNPs that were significantly associated with CHD in the genome-wide scan were assayed in a second set of cases and controls and analyzed using Chi-square tests and permutation testing. For the remaining data sets, case-control differences in allele frequencies of rs10757274 and rs2383206 were evaluated using chi-square tests on 3×2 contingency tables. Population attributable risk was calculated using the formula PAR=I(T)−1(0), where 1(T) is the total disease incidence in the population, and 1(0) is the disease incidence in unexposed individuals.

TABLE 1

Clinical Characteristics of Participants in the Ottawa Heart Study.

|  | Early CHD Cases | Healthy Controls |
| --- | --- | --- |
| OHS-1* | | |
| n | 322 | 312 |
| Men (%) | 90 | 55 |
| Controls: Age at Recruitment | N/A | 69.0 ± 6.1 |
| Cases: Age at Diagnosis | 48.5 ± 7.2 | N/A |
| MI (%) | 62 | 0 |
| PCI (%) | 57 | 0 |
| CABG (%) | 74 | 0 |
| Cholesterol (mg/dL) | 218.9 ± 34.4 | 216.9 ± 36.7 |
| Triglycerides (mg/dL) | 215.2 ± 124.9 | 128.4 ± 71.7 |
| LDL-C (mg/dL) | 137.7 ± 30.9 | 135.3 ± 32.1 |

TABLE 1-continued

Clinical Characteristics of Participants in the Ottawa Heart Study.

| | Early CHD Cases | Healthy Controls |
|---|---|---|
| HDL-C (mg/dL) | 40.2 ± 15.1 | 56.5 ± 15.1 |
| Hypertension (%) | 37 | 33 |
| Cigarette Smoking, ever (%) | 60 | 36 |
| BMI (kg/m$^2$) | 28.5 ± 4.1 | 28.0 ± 6.3 |
| OHS-2[†] | | |
| n | 311 | 326 |
| Men (%) | 80 | 74% |
| Controls: Age at Recruitment | N/A | 70.6 ± 6.4 |
| Cases: Age at Diagnosis | 47.5 ± 7.2 | N/A |
| MI (%) | 65 | 0 |
| PCI (%) | 53 | 0 |
| CABG (%) | 59 | 0 |
| Cholesterol (mg/dL) | 226.6 ± 39.1 | 220.8 ± 37.1 |
| Triglycerides (mg/dL) | 225.9 ± 162.1 | 138.2 ± 101.9 |
| LDL-C (mg/dL) | 144.2 ± 36.3 | 141.5 ± 31.7 |
| HDL-C (mg/dL) | 41.0 ± 13.1 | 53.0 ± 18.2 |
| Hypertension (%) | 44 | 23 |
| Cigarette smoking, ever (%) | 55 | 16 |
| BMI (kg/m$^2$) | 28.8 ± 4.7 | 26.1 ± 3.7 |
| OHS-3[‡] | | |
| n | 647 | 847 |
| Men (%) | 76 | 61 |
| Controls: Age at recruitment | N/A | 72.5 ± 6.0 |
| Cases: Age at diagnosis | 49.6 ± 8.3 | N/A |
| MI (%) | 66 | 0 |
| PCI (%) | 60 | 0 |
| CABG (%) | 58 | 0 |
| Cholesterol (mg/dL) | 231.6 ± 39.8 | 223.5 ± 40.6 |
| Triglycerides (mg/dL) | 194.0 ± 129.3 | 128.5 ± 88.6 |
| LDL-C (mg/dL) | 148.1 ± 35.9 | 141.9 ± 33.2 |
| HDL-C (mg/dL) | 45.6 ± 13.5 | 55.3 ± 17.0 |
| Hypertension (%) | 43 | 32 |
| Cigarette smoking, ever (%) | 67 | 44 |
| BMI (kg/m$^2$) | 28.6 ± 4.9 | 26.4 ± 4.0 |

Lipid values, ages and BMI are expressed as means ± SD.
*Lipid values prior to treatment with lipid modifying agents; n = 277 cases, n = 285 controls.
[†]Lipid values prior to treatment with lipid modifying agents; n = 195 cases, n = 284 controls
[‡]Clinical data for 580 cases and 822 controls. Lipid values prior to treatment with lipid modifying agents; n = 249 cases, n = 418 controls,
MI, myocardial infarction;
PCI, percutaneous coronary intervention;
CABG, coronary artery bypass grafting;
LDL-C, low density lipoprotein-cholesterol;
HDL-C, high density lipoprotein-cholesterol;
BMI, body mass index

TABLE 2

SNPs associated with CHD in OHS-1, OHS-2 and ARIC. The P-values for the number of SNPs observed relative to the number expected were derived from 1000 permutations in which case-control status was randomized. SNPs in the ARIC cohort were tested for association with incident CHD. Individuals with prevalent CHD at baseline were excluded.

| Cohort | SNPs Assayed (n) | SNPs with P < 0.025 Observed (n) | SNPs with P < 0.025 Expected (n) | Observed-Expected (n) | P |
|---|---|---|---|---|---|
| OHS-1 | 72,864 | 2,586 | 2,066 | 520 | <0.001 |
| OHS-2 | 2,083 | 50 | 26 | 24 | <0.001 |
| ARIC | 50 | 2 | 0 | 2 | NA |

OHS, Ottawa Heart Study;
ARIC, Atherosclerosis Risk in Communities Study;
SNP, single nucleotide polymorphism

TABLE 3

Association between SNPs rs10757274 and rs2383206 and CHD.

| | rs10757274 | | | | | | | rs2383206 | | | | | | |
|---|---|---|---|---|---|---|---|---|---|---|---|---|---|---|
| | Controls | | | Cases | | | | Controls | | | Cases | | | |
| Cohort | AA | AG | GG | AA | AG | GG | $\chi^2$-P | HW-P | AA | AG | GG | AA | AG | GG | $\chi^2$-P | HW-P |
| OHS-1 | 85 | 149 | 78 | 49 | 148 | 125 | 3.7 × 10$^{-6}$ | 0.08 | 77 | 147 | 88 | 45 | 140 | 137 | 6.7 × 10$^{-6}$ | 0.19 |
| OHS-2 | 85 | 161 | 80 | 56 | 140 | 108 | 0.0009 | 0.4 | 80 | 160 | 86 | 50 | 141 | 113 | 0.0008 | 0.34 |
| ARIC | 2063 | 3822 | 1858 | 230 | 525 | 282 | 0.004 | 0.11 | 2140 | 4161 | 2231 | 230 | 600 | 324 | 0.0007 | 0.21 |
| CCHS | 2752 | 4543 | 1758 | 393 | 792 | 340 | 0.0004 | 0.56 | 2489 | 4583 | 1981 | 372 | 782 | 371 | 0.016 | 0.58 |
| DHS | 147 | 258 | 122 | 27 | 85 | 42 | 0.025 | 0.99 | 131 | 258 | 138 | 24 | 84 | 46 | 0.045 | 0.95 |
| OHS-3 | 228 | 418 | 201 | 121 | 333 | 193 | 0.0003 | 0.96 | 197 | 416 | 229 | 115 | 327 | 209 | 0.011 | 0.98 |

Values are numbers of individuals in each genotype group.

P-values were calculated by Chi-Square tests on allele counts.

OHS, Ottawa Heart Study,

ARIC, Atherosclerosis Risk in Communities Study;

CCHS, Copenhagen City Heart Study,

DHS, Dallas Heart Study,

SNP, single nucleotide polymorphism.

TABLE 4

Risk of CHD as a function of rs10757274 and rs2383206 in the Atherosclerosis Risk in Communities Study and the Copenhagen City Heart Study.

| | Atherosclerosis Risk in Communities Study | | | | | Copenhagen City Heart Study | | | | |
|---|---|---|---|---|---|---|---|---|---|---|
| | | Number of Events | | | | | Number of Events | | | |
| | n (%) | Observed | Expected[1] | Incidence[2] | Hazard Ratio | n (%) | Observed | Expected | Incidence | Hazard Ratio |
| rs10757274 | | | | | | | | | | |
| AA | 2,293 (26) | 255[3] | 295 | 79 (70-89) | 1 | 3,145 (30) | 393[5] | 473 | 61 (55-68) | 1 |
| AG | 4,347 (50) | 564 | 553 | 93 (86-101) | 1.18 (1.02-1.37) | 5,335 (50) | 792 | 755 | 73 (68-79) | 1.26 (1.12-1.42) |
| GG | 2,140 (24) | 298 | 269 | 101 (90-114) | 1.29 (1.09-1.52) | 2,098 (20) | 340 | 296 | 80 (72-89) | 1.38 (1.19-1.60) |
| rs2383206 | | | | | | | | | | |
| AA | 2,370 (25) | 259[4] | 310 | 78 (69-88) | 1 | 2,861 (27) | 372[6] | 425 | 64 (58-71) | 1 |
| AG | 4,761 (49) | 643 | 610 | 97 (90-105) | 1.26 (1.09-1.46) | 5,365 (51) | 782 | 772 | 72 (67-77) | 1.16 (1.02-1.31) |
| GG | 2,555 (26) | 345 | 327 | 97 (88-108) | 1.26 (1.07-1.48) | 2,352 (22) | 371 | 327 | 78 (71-87) | 1.29 (1.12-1.50) |

[1]Based on the Log-rank test.
[2]Incidence rate measured in number of events per 10,000 person years of follow-up.
[3]$p < 0.0111$
[4]$p < 0.0041$.
[5]$p < 0.00001$.
[6]$p < 0.0$

TABLE 5

Clinical and laboratory characteristics of participants in the ARIC Study.

| | rs10757274 | | | | rs2383206 | | | |
|---|---|---|---|---|---|---|---|---|
| | AA | AG | GG | P-value | AA | AG | GG | P-value |
| n | 2,293 | 4,347 | 2,140 | — | 2,370 | 4,761 | 2,555 | — |
| Men/Women | 1,057/1,236 | 1,972/2,375 | 958/1,182 | 0.67 | 1,106/1,264 | 2,160/2,601 | 1,152/1,403 | 0.48 |
| Age (years) | 54 ± 6 | 54 ± 6 | 54 ± 6 | 0.76 | 54 ± 6 | 54 ± 6 | 54 ± 6 | 0.09 |
| BMI (kg/m$^2$) | 27.2 ± 5.0 | 26.9 ± 4.8 | 26.8 ± 4.7 | 0.004 | 27.2 ± 5.0 | 26.9 ± 4.8 | 26.9 ± 4.8 | 0.01 |
| Systolic BP (mm/Hg) | 119 ± 17 | 118 ± 17 | 118 ± 17 | 0.44 | 119 ± 17 | 118 ± 17 | 118 ± 17 | 0.53 |
| Diastolic BP (mm/Hg) | 72 ± 10 | 72 ± 10 | 71 ± 10 | 0.28 | 72 ± 10 | 71 ± 10 | 72 ± 10 | 0.06 |
| Glucose (mg/dL) | 106 ± 33 | 105 ± 32 | 104 ± 25 | 0.07 | 105 ± 30 | 105 ± 32 | 104 ± 26 | 0.29 |
| Cholesterol (mg/dL) | 215 ± 39 | 215 ± 41 | 213 ± 40 | 0.16 | 214 ± 39 | 215 ± 41 | 213 ± 40 | 0.17 |
| Triglyceride (mg/dL) | 116 (82-167) | 112 (80-160) | 112 (80-162) | 0.16 | 115 (82-166) | 112 (81-160) | 113 (81-162) | 0.28 |
| LDL-C (mg/dL) | 137 ± 37 | 137 ± 38 | 135 ± 37 | 0.23 | 137 ± 37 | 137 ± 39 | 136 ± 37 | 0.27 |
| HDL-C (mg/dL) | 51 ± 17 | 51 ± 17 | 51 ± 16 | 0.56 | 51 ± 17 | 51 ± 17 | 51 ± 16 | 0.16 |

Values are means ± standard deviations, except for triglycerides which are medians (interquartile ranges).
P-values were calculated using ANOVA.
Variables with highly skewed distributions (triglycerides) were log transformed prior to analysis.
BMI, body mass index;
BP, blood pressure;
LDL-C, low density lipoprotein-cholesterol;
HDL-C, high density lipoprotein-cholesterol.
In addition to the above analyses, both SNPs remained significant in models that included (and excluded) the following co-variates: age, gender, plasma lipid levels, hypertension status, blood pressure levels, diabetes status, glucose and insulin levels, measures of body size (including waist circumference and BMI), measures of inflammation (including CRP, sICAM and sVCAM), environmental exposures including smoking, diet (e.g. saturated fat intake and Key's score) and physical activity (work and recreational).

TABLE 6

Clinical and laboratory characteristics of participants in the Copenhagen City Heart Study.

| | rs10757274 | | | | rs2383206 | | | |
|---|---|---|---|---|---|---|---|---|
| | AA | AG | GG | P-value | AA | AG | GG | P-value |
| n | 3,145 | 5,335 | 2,098 | — | 2,861 | 5,365 | 2,352 | — |
| Men/Women | 1,358/1,787 | 2,401/2,934 | 952/1146 | 0.18 | 1,233/1,628 | 2,395/2,970 | 1,083/1,269 | 0.10 |
| Age (years) | 58 ± 15 | 57 ± 15 | 57 ± 15 | 0.29 | 58 ± 12 | 58 ± 15 | 57 ± 15 | 0.10 |
| BMI (kg/m$^2$) | 26 ± 4 | 26 ± 4 | 26 ± 4 | 0.57 | 25 ± 4 | 26 ± 4 | 26 ± 4 | 0.24 |
| Systolic BP (mm/Hg) | 139 ± 23 | 138 ± 22 | 139 ± 23 | 0.59 | 139 ± 23 | 139 ± 22 | 139 ± 23 | 0.96 |
| Diastolic BP (mm/Hg) | 84 ± 12 | 84 ± 12 | 84 ± 12 | 0.38 | 84 ± 12 | 84 ± 12 | 84 ± 12 | 0.22 |
| Glucose (mg/dL) | 104 ± 34 | 105 ± 36 | 105 ± 34 | 0.35 | 105 ± 35 | 105 ± 35 | 105 ± 34 | 0.60 |

TABLE 6-continued

Clinical and laboratory characteristics of participants in the Copenhagen City Heart Study.

| | rs10757274 | | | | rs2383206 | | | |
|---|---|---|---|---|---|---|---|---|
| | AA | AG | GG | P-value | AA | AG | GG | P-value |
| Cholesterol (mg/dL) | 237 ± 50 | 238 ± 49 | 236 ± 52 | 0.40 | 237 ± 50 | 238 ± 49 | 236 ± 52 | 0.29 |
| Triglyceride (mg/dL) | 135 (96-202) | 133 (96-196) | 137 (96-194) | 0.98 | 135 (96-202) | 136 (96-196) | 137 (96-194) | 0.88 |
| LDL-C (mg/dL) | 161 ± 48 | 162 ± 47 | 161 ± 47 | 0.43 | 161 ± 48 | 162 ± 47 | 161 ± 47 | 0.40 |
| HDL-C (mg/dL) | 61 ± 19 | 61 ± 19 | 60 ± 19 | 0.64 | 61 ± 19 | 61 ± 19 | 60 ± 19 | 0.41 |

Values are means ± standard deviations, except for triglycerides which are medians (interquartile ranges).
P-values were calculated using ANOVA.
Variables with highly skewed distributions (triglycerides) were log transformed prior to analysis.
BMI, body mass index;
BP, blood pressure;
LDL-C, low density lipoprotein-cholesterol;
HDL-C, high density lipoprotein-cholesterol

TABLE 7

Sequence variations identified in the 58 kd risk interval on chromosome 9 in two individuals homozygous for the risk allele and one homozygous for the alternate allele.

| | | Allele | | Risk Genotype | | Referent Genotype |
|---|---|---|---|---|---|---|
| Position | Type | Major | Minor | 1 | 2 | 1 |
| 22062264 | SNP | A | G | G/G | G/G | A/A |
| 22062301 | SNP | G | C | C/C | C/C | G/G |
| 22062638 | SNP | G | A | A/A | A/A | G/G |
| 22062719 | SNP | A | G | G/G | G/G | A/A |
| 22063996 | SNP | T | G | G/G | G/G | N/N |
| 22067543 | SNP | C | T | T/T | T/T | N/N |
| 22071397 | SNP | G | T | T/T | T/T | G/G |
| 22071850 | SNP | C | T | T/T | T/T | C/C |
| 22072375 | SNP | A | C | A/C | A/A | A/A |
| 22073209 | SNP | C | T | C/C | C/T | N/N |
| 22073400 | SNP | A | T | A/T | A/A | N/N |
| 22073404 | SNP | C | T | T/T | T/T | N/N |
| 22074310 | SNP | C | T | T/T | T/T | N/N |
| 22075598 | SNP | T | C | C/C | C/C | N/N |
| 22077473 | SNP | T | C | C/C | C/C | C/T |
| 22078090 | SNP | A | T | T/T | T/T | A/A |
| 22073094 | SNP | A | G | G/G | G/G | A/A |
| 22078260 | SNP | C | T | T/T | T/T | C/C |
| 22078465 | DEL | CA | — | —/— | —/— | CA/CA |
| 22089568 | SNP | C | A | A/A | A/A | N/N |
| 22089755 | INS | — | A | A/A | A/A | —/— |
| 22090176 | SNP | G | C | C/C | C/C | G/G |
| 22091702 | SNP | T | C | C/C | C/C | T/T |
| 22092165 | SNP | C | T | T/T | T/T | C/C |

TABLE 7-continued

Sequence variations identified in the 58 kd risk
interval on chromosome 9 in two individuals homozygous
for the risk allele and one homozygous for the alternate allele.

| Position | Type | Allele Major | Allele Minor | Risk Genotype 1 | Risk Genotype 2 | Referent Genotype 1 |
|---|---|---|---|---|---|---|
| 22092437 | SNP | G | A | G/G | G/G | A/G |
| 22093183 | SNP | G | T | T/T | T/T | G/G |
| 22093341 | SNP | T | G | G/G | G/G | T/T |
| 22093813 | SNP | A | G | G/G | G/G | A/A |
| 22095927 | SNP | T | C | C/C | C/C | T/T |
| 22096225 | SNP | G | A | A/A | A/A | N/N |
| 22096271 | SNP | A | G | G/G | G/G | N/N |
| 22096400 | SNP | G | A | A/G | G/G | N/N |
| 22096731 | SNP | T | A | A/A | A/A | T/T |
| 22097238 | SNP | A | T | A/A | A/A | A/T |
| 22100131 | SNP | T | C | C/C | C/C | T/T |
| 22101587 | INS | — | TTGAT | TTGAT/TTGAT | TTGAT/TTGAT | —/— |
| 22102241 | SNP | A | C | C/C | C/C | A/A |
| 22102427 | SNP | A | G | G/G | G/G | A/A |
| 22102599 | SNP | T | C | C/C | C/C | N/N |
| 22104469 | SNP | G | C | C/C | C/C | G/G |
| 22104495 | SNP | A | G | G/G | G/G | A/A |
| 22105026 | SNP | A | G | G/G | G/G | A/A |
| 22105286 | SNP | T | C | C/C | C/C | T/T |
| 22105589 | SNP | A | T | T/T | T/T | N/N |
| 22105959 | SNP | A | G | G/G | G/G | A/G |
| 22106046 | SNP | A | G | G/G | G/G | A/A |
| 22106071 | SNP | T | C | C/C | C/C | C/T |
| 22106220 | SNP | T | C | C/C | C/C | T/T |
| 22107781 | SNP | C | T | C/T | C/C | C/C |
| 22110491 | INS | — | T | T/T | T/T | —/— |
| 22110813 | DEL | CAT | — | —/— | —/— | CAT/— |
| 22113766 | SNP | A | C | C/C | C/C | A/A |
| 22114123 | SNP | T | A | A/A | A/A | T/T |
| 22114140 | SNP | A | T | T/T | T/T | A/A |
| 22115347 | SNP | A | C | C/C | C/C | A/A |

TABLE 7-continued

Sequence variations identified in the 58 kd risk
interval on chromosome 9 in two individuals homozygous
for the risk allele and one homozygous for the alternate allele.

|  |  | Allele | | Risk Genotype | | Referent Genotype |
|---|---|---|---|---|---|---|
| Position | Type | Major | Minor | 1 | 2 | 1 |
| 22115503 | SNP | G | C | C/C | C/C | G/G |
| 22115913 | SNP | C | T | T/T | T/T | N/N |
| 22117613 | SNP | C | T | C/T | C/C | C/C |
| 22117641 | SNP | G | A | A/G | G/G | G/G |
| 22117879 | SNP | A | G | A/G | A/G | A/A |
| 22118166 | INS | — | AT | AT/— | AT/— | —/— |
| 22118600 | SNP | G | A | A/G | A/G | N/N |
| 22118730 | SNP | C | G | C/G | C/C | N/N |
| 22119594 | SNP | G | C | C/C | C/C | C/C |
| 22119721 | INS | — | T | T/T | T/— | T/T |
| 22120389 | SNP | A | T | A/T | A/T | A/A |

TABLE 8

Allele frequencies of chromosome 9 sequence
variants associated with CHD in Caucasians.

| | | Minor Allele Frequency | |
|---|---|---|---|
| SNP ID | Position | Caucasians | African-Americans |
| rs9632884 | 22062301 | 0.48 | 0.008 |
| rs6475606 | 22071850 | 0.5 | 0.008 |
| rs10757272 | 22078260 | 0.5 | 0.15 |
| rs10757274 | 22086055 | 0.49 | 0.21 |
| rs4977574 | 22088574 | 0.5 | 0.08 |
| rs2891168 | 22088619 | 0.5 | 0.08 |
| rs1333042 | 22093813 | 0.49 | 0.008 |
| rs2383206 | 22105026 | 0.49 | 0.41 |
| rs1333048 | 22115347 | 0.49 | 0.25 |
| rs1333049 | 22115503 | 0.49 | 0.175 |

TABLE 9

Association between rs10757274 and rs2383206 and CHD in African-Americans in ARIC and DHS.

| | rs10757274 | | | | | | | rs2383206 | | | | | | |
|---|---|---|---|---|---|---|---|---|---|---|---|---|---|---|
| | Controls | | | Cases | | | | Controls | | | Cases | | | |
| Cohort | AA | AG | GG | AA | AG | GG | P | AA | AG | GG | AA | AG | GG | P |
| ARIC | 1857 | 971 | 143 | 187 | 92 | 14 | 0.90 | 1019 | 1532 | 541 | 114 | 161 | 46 | 0.32 |
| DHS | 447 | 251 | 32 | 175 | 66 | 21 | 0.64 | 231 | 371 | 129 | 90 | 123 | 48 | 0.67 |

Values in the table are numbers of individuals.

P values were calculated using Chi-square tests.

ARIC, Atherosclerosis Risk in Communities Study;

DHS, Dallas Heart Study.

Cases and controls are defined as indicated in the Methods.

TABLE 10

| Position | Type | rs No. | Risk Allele | MAF |
|---|---|---|---|---|
| 22062264 | SNP | rs10757269 | G | 0.478 |
| 22062301 | SNP | rs9632884 | C | 0.478 |
| 22062638 | SNP | rs9632885 | A | |
| 22062719 | SNP | rs10757270 | G | |
| 22071397 | SNP | rs10116277 | T | 0.494 |
| 22071850 | SNP | rs6475606 | T | 0.494 |
| 22078090 | SNP | rs10738606 | T | |
| 22078094 | SNP | rs10738607 | G | 0.494 |
| 22078260 | SNP | rs10757272 | T | |
| 22078465 | DEL | | — | |
| 22086055 | SNP | rs10757274 | G | |
| 22088574 | SNP | rs4977574 | G | |
| 22088619 | SNP | rs2891168 | G | |
| 22089755 | INS | | | |
| 22090176 | SNP | rs1556516 | C | 0.494 |
| 22091702 | SNP | rs6475608 | C | 0.233 |
| 22092165 | SNP | rs7859727 | T | 0.500 |
| 22093183 | SNP | rs1537372 | T | |
| 22093341 | SNP | rs1537373 | G | 0.494 |
| 22093813 | SNP | rs1333042 | G | 0.489 |
| 22095927 | SNP | | C | |
| 22096731 | SNP | rs1333043 | A | 0.47 |
| 22100131 | SNP | rs1412834 | C | 0.472 |
| 22101587 | INS | | TTGAT | |
| 22102241 | SNP | rs7341786 | C | 0.467 |
| 22102427 | SNP | rs7341791 | G | |
| 22104469 | SNP | rs10733376 | C | 0.478 |
| 22104495 | SNP | rs10738609 | G | 0.472 |
| 22105026 | SNP | rs2383206 | G | 0.472 |
| 22105286 | SNP | rs944797 | C | 0.472 |
| 22106046 | SNP | rs1537374 | G | 0.472 |
| 22106220 | SNP | rs1537376 | C | |
| 22110491 | INS | | T | |
| 22113766 | SNP | rs10738610 | C | 0.478 |
| 22114123 | SNP | rs1333046 | A | 0.478 |
| 22114140 | SNP | rs7857118 | T | |
| 22115347 | SNP | rs1333048 | C | 0.483 |
| 22115503 | SNP | rs1333049 | C | 0.500 |

MAF, minor allele frequency in the European (CEU) HapMap panel.

TABLE 11

| POSITION | rs No. | MAF |
|---|---|---|
| 22062730 | rs17761197 | 0.000 |
| 22063170 | rs10965226 | 0.000 |
| 22063334 | rs16923583 | 0.000 |
| 22064793 | rs7855162 | 0.000 |
| 22066071 | rs1831733 | |
| 22066208 | rs1831734 | |
| 22066795 | rs10757271 | |
| 22067085 | rs10811652 | |
| 22068305 | rs7855660 | 0.000 |
| 22069020 | rs6475605 | 0.000 |
| 22070363 | rs16905613 | 0.006 |
| 22070791 | rs7858034 | 0.000 |
| 22071128 | rs12347950 | 0.000 |
| 22071346 | rs1412833 | |
| 22071796 | rs10965227 | 0.262 |
| 22072340 | rs1547704 | 0.000 |
| 22072380 | rs10965228 | 0.097 |
| 22073017 | rs7853953 | 0.000 |
| 22074633 | rs10122192 | 0.000 |
| 22076840 | rs10120722 | 0.000 |
| 22076883 | rs16905635 | 0.000 |
| 22078556 | rs16905640 | 0.000 |
| 22078937 | rs13300638 | |
| 22079014 | rs13284693 | 0.000 |
| 22079193 | rs12235973 | |
| 22080301 | rs10757273 | |
| 22080416 | rs10965230 | |
| 22080416 | rs35573493 | |
| 22080521 | rs9644859 | |
| 22080521 | rs35170871 | |
| 22080603 | rs9644860 | |
| 22080603 | rs34933796 | |
| 22080683 | rs7019916 | |
| 22080753 | rs7020031 | |
| 22080811 | rs7034707 | |
| 22081731 | rs12005039 | |
| 22081731 | rs34597771 | |
| 22081924 | rs7866503 | |
| 22081924 | rs34555767 | |
| 22081924 | rs11506225 | |
| 22082097 | rs7869527 | |
| 22082257 | rs2210538 | |
| 22082257 | rs11506451 | |
| 22082551 | rs7870178 | |
| 22082670 | rs9776546 | |
| 22082924 | rs11532910 | |
| 22082924 | rs10811654 | |
| 22082924 | rs34184423 | |
| 22083299 | rs34168773 | |
| 22084281 | rs7848875 | 0.000 |
| 22084330 | rs35537809 | |
| 22084330 | rs7388840 | |
| 22084330 | rs4977757 | |
| 22084796 | rs10738608 | |
| 22085567 | rs35869261 | |
| 22086055 | rs10757274 | |
| 22087022 | rs16905644 | 0.000 |
| 22087693 | rs6475607 | 0.006 |
| 22088038 | rs7037832 | 0.000 |
| 22088374 | rs133304 | |
| 22088574 | rs4977574 | 0.494 |
| 22088619 | rs2891168 | 0.494 |
| 22088674 | rs10965231 | 0.000 |
| 22088683 | rs11787814 | |
| 22089940 | rs7856476 | 0.000 |
| 22090726 | rs12238050 | 0.000 |
| 22091120 | rs10965232 | 0.000 |
| 22091259 | rs132929384 | 0.000 |
| 22091435 | rs7028026 | |
| 22092128 | rs10125231 | 0.022 |
| 22093314 | rs10965233 | 0.000 |
| 22093748 | rs7022719 | 0.000 |
| 22094450 | rs4336695 | 0.000 |
| 22095595 | rs7872591 | 0.000 |
| 22098069 | rs7855190 | 0.000 |
| 22098942 | rs10217720 | |
| 22099387 | rs10217426 | 0.000 |
| 22100478 | rs17761319 | 0.000 |
| 22101973 | rs16905648 | 0.000 |
| 22102606 | rs17834367 | 0.006 |
| 22102943 | rs7032115 | 0.000 |
| 22103324 | rs13301964 | 0.011 |
| 22103924 | rs16905652 | 0.000 |
| 22105078 | rs10965234 | 0.000 |
| 22105105 | rs10965235 | 0.000 |
| 22105217 | rs4990722 | 0.000 |
| 22105285 | rs944796 | 0.000 |
| 22105633 | rs10965236 | 0.000 |
| 22107669 | rs7851006 | |
| 22108026 | rs17834457 | 0.000 |
| 22108102 | rs17761446 | 0.000 |
| 22108378 | rs7854631 | 0.000 |
| 22108481 | rs4977758 | 0.000 |
| 22108885 | rs4977759 | 0.000 |
| 22109128 | rs1333044 | 0.000 |
| 22109195 | rs1333045 | 0.442 |
| 22111167 | rs12685422 | 0.000 |
| 22111349 | rs10217586 | |
| 22111353 | rs7860589 | |
| 22112193 | rs7020671 | |
| 22112530 | rs10965237 | 0.000 |
| 22112912 | rs13285121 | |
| 22113590 | rs7869069 | 0.000 |
| 22113967 | rs7854016 | 0.000 |
| 22114368 | rs17761458 | 0.000 |
| 22114450 | rs10757277 | |
| 22114472 | rs10811656 | |
| 22114477 | rs10757278 | 0.488 |

TABLE 11-continued

| POSITION | rs No. | MAF |
|---|---|---|
| 22114504 | rs1333047 | 0.500 |
| 22114630 | rs10757279 | |
| 22114744 | rs4977575 | 0.500 |
| 22116454 | rs12345199 | 0.000 |
| 22116885 | rs12336106 | 0.000 |
| 22117777 | rs17834529 | |
| 22117883 | rs10965238 | 0.030 |
| 22117965 | rs10965239 | 0.000 |
| 22118180 | rs12379111 | 0.138 |
| 22118709 | rs12347779 | 0.089 |
| 22119164 | rs10965240 | 0.011 |
| 22119579 | rs7020996 | 0.194 |
| 22120065 | rs10965243 | 0.144 |

MAF, minor allele frequency in the European (CEU) HapMap panel.

REFERENCES CITED IN THE EXAMPLE

1. C. J. Murray, A. D. Lopez, Lancet 349, 1436 (1997).
2. C. D. Mathers, D. Loncar, PLoS Med 3, e442 (2006).
3. S. F. Saccone et al., Hum Mol Genet 16, 36 (2007).
4. The ARIC Study Investigators, Am J Epidemiol 129, 687 (1989)
5. P. Schnohr, G. Jensen, H. Scharling, M. Appleyard, Eur Heart J 3, Suppl H., H1 (2001).
6. R. G. Victor et al., Am J Cardiol 93, 1473 (2004).
7. A. S. Agatston et al., J Am Coll Cardiol 15, 827 (1990).
8. E. Pasmant, Laurendeau, I., Heron, D., Vidaud, M., Vidaud, D., Bieche, I., Cancer Res 67, 1 (2007).
9. J. Cohen et al., Proc Natl Acad Sci USA 103, 1810 (2006).
10. J. C. Cohen, E. Boerwinkle, T. H. Mosley, H. H. Hobbs, N. Engl. J. Med. 354, 34 (2006).
11. S. Romeo et al., Nat Genet 39, 513 (2007).
12. Circulation 106, 3143 (2002).
13. The ARIC Study Investigators, Am J Epidemiol 129, 687 (1989).
14. L. E. Chambless et al., J Clin Epidemiol 56, 880 (2003).
15. S. A. Brown et al., Arteriscler. Thromb 13, 1139 (1993).
16. P. Schnohr, G. Jensen, H. Scharling, M. Appleyard, Eur Heart J 3, Suppl H., H1 (2001).
17. T. Jain et al., J. Am Coll Cardiol 44, 1011 (2004, 2004).
18. N. Patil et al., Science 294, 1719 (2001).
19. M. Tartaglia et al., Nat Genet 39, 75 (2007).

EQUIVALENTS

The examples and detailed description herein are offered by way of illustration and not by way of limitation. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

The invention claimed is:

1. A method for reducing risk of coronary atherosclerosis in a human, the method comprising:
   a) determining a human has a 'G' allele or its complement at the polymorphic position defined by rs10757274; and
   b) administering to the human a therapy to delay the onset, prevent the onset or slow the progression of the coronary atherosclerosis.

2. The method of claim 1, wherein the human is homozygous for said 'G' allele or its complement.

3. The method of claim 1, wherein the human is heterozygous for said 'G' allele or its complement.

4. The method of claim 1, wherein the therapy is a lipid-lowering medication.

* * * * *